(12) United States Patent
Bujard et al.

(10) Patent No.: US 7,666,668 B2
(45) Date of Patent: Feb. 23, 2010

(54) CHROMOSOMAL LOCI FOR THE STRINGENT CONTROL OF GENE ACTIVITIES VIA TRANSCRIPTION ACTIVATION SYSTEMS

(75) Inventors: Hermann Bujard, Heidelberg (DE); Kai Schönig, Heidelberg (DE)

(73) Assignee: TET Systems Holding GmbH & Co. KG, Heidelberg (DE)

( * ) Notice: Subject to any disclaimer, the term of this patent is extended or adjusted under 35 U.S.C. 154(b) by 453 days.

(21) Appl. No.: 10/525,785

(22) PCT Filed: Aug. 6, 2003

(86) PCT No.: PCT/EP03/08713

§ 371 (c)(1),
(2), (4) Date: Sep. 14, 2005

(87) PCT Pub. No.: WO2004/020645

PCT Pub. Date: Mar. 11, 2004

(65) Prior Publication Data

US 2008/0141386 A1    Jun. 12, 2008

Related U.S. Application Data

(60) Provisional application No. 60/406,344, filed on Aug. 28, 2002.

(51) Int. Cl.
C07H 21/04 (2006.01)
C12N 15/00 (2006.01)
C12N 15/10 (2006.01)
C12N 15/64 (2006.01)

(52) U.S. Cl. .................. 435/320.1; 435/91.4; 536/23.1

(58) Field of Classification Search ................ 536/23.1; 435/91.4, 320.1
See application file for complete search history.

(56) References Cited

U.S. PATENT DOCUMENTS 6,242,667 B1 * 6/2001 Bujard et al. ............... 800/278

FOREIGN PATENT DOCUMENTS

EP    1 092 771    4/2001

OTHER PUBLICATIONS

Entrez Nucleotide Database entry for Accession No. AC122286, updated Nov. 25, 2003, downloaded Jun. 18, 2008.*
Osoegawa et al. (2000) Genome Res. 10:116-128.*
SEQ ID Search Results (Zhao et al, 2000; Konno et al, 2000; The Joint Genome Institute, 2000; Zhao et al, 2000).*
Cameron, Mol. Biotech. 7(3):253-265, 1997.*
Marth et al, Nature Genetics 23:452-456, 1999.*
Wheelan et al, Genome Res. 11:1952-1957, 2001.*
Baron, U. et al.: "Co-regulation of two gene activities by tetracycline via a bidirectional promoter," Nucleic Acids Research, Oxford University Press, Surrey, GB, vol. 23, No. 17, Sep. 11, 1995, pp. 3605-3606.
St-Onge, L. et al.: "Temporal control of the Cre recombinase in transgenic mice by a tetracycline responsive promoter," Nucl. Acids Res., vol. 24, No. 19, 1996, pp. 3875-3877.
Database EBI DNA Sequences 'Online!, Jun. 2, 2002, "Mus musculus BAC clone RP23-111G16 from chromosome 6," retrieved from EBI Database accession No. AC122874.

* cited by examiner

*Primary Examiner*—Kevin K. Hill
(74) *Attorney, Agent, or Firm*—Weingarten, Schurgin, Gagnebin & Lebovici LLP

(57) ABSTRACT

The invention relates to a method for obtaining a chromosomal locus for transgenesis of a multicellular eukaryotic organism, "MEO", to a vector for transgenesis by homologous recombination of a MEO and to the use of such an vector for trans-genesis by homologous recombination of a MEO and to the transgenic MEO thus obtainable.

6 Claims, 12 Drawing Sheets

A

B

A

① E11, pBeloBAC primer 3

② Subclone 5, pBeloBAC primer 3

③ subclone BAC22. T7 primer

④ subclone BAC18. T7 primer

C chromosome 6 position of E11 region

Figure 4:
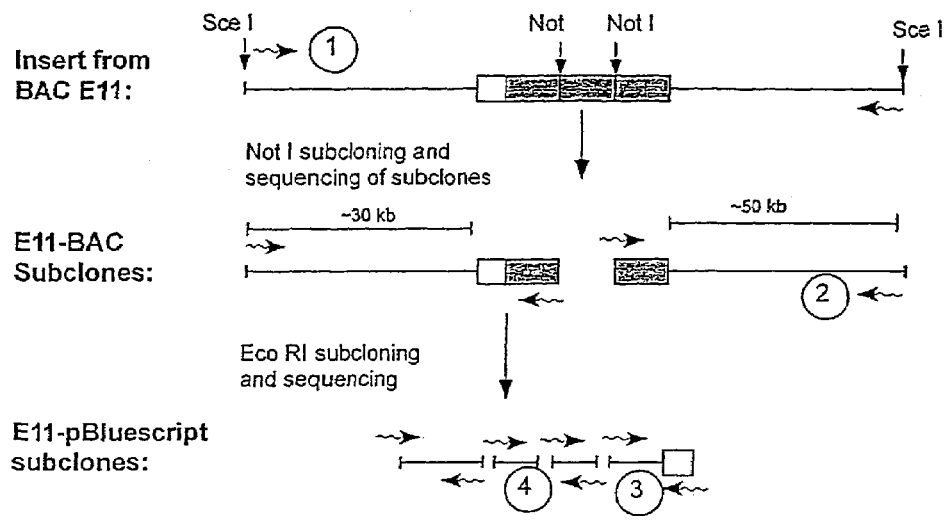
Figure 4:
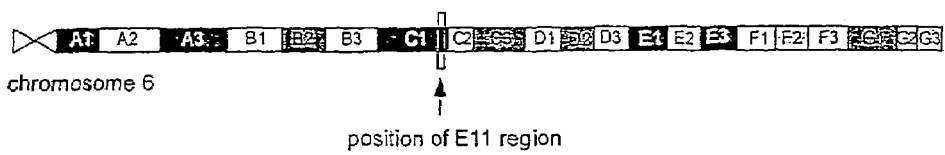

Fig 4 B.
Sequence 1. (SEQ ID No.1) : E11, pBeloBAC primer 3 :

TAAAGGGAAATCCACAATTTAAAATGTGACAGAAATTTATGATTGTTTTTATTTAAATGTT
TATCTTTTCAAGAAATATCACGTGTAATGTATTTCAAAATGTCTCCTAGAAAAGTGCATGA
CTCTGCGAAGGAGAGAGTTGGTGGGGGAGAGTCAGGAAAATGTAGAGGGGCAACAATGTAG
AAATTATGGAAAATGAAATTAATA

Score = 1005 (150.8 bits), Expect = 4.2e-51, Sum P(13) = 4.2e-51, Identities = 207/210 (99%), Positives = 207/210 (99%), Strand = Minus / Plus Sequence 2. (SEQ ID No.2): Subclone 5, pBeloBAC primer 3 :
ACTATACCATACTTGATTTAAACATATTAGCAGTTTCTCTCCTTCATTATGTACTCCGCT
AAATTTGAATATGAAACCATTCTTGTACCACTGACAGTTGGCAGAAAGTTTACTTTATAA
ACACATTTTTAAGCATGTGTATATGTATGTGTATGTGTGGTTATGTGTACAGAATTGCAA
GTGCCCCAAGAGACCCTAGGTCTGGAGTTACAGGTGGCTGTAAGGTGGCAATTGAACTCT
GATCCTCTGCAAGGGCATGCATGCTCTTAACCATTGAGCCATCCCTACTGCCTGGCAACA
AGTTTTTGATAGCAACTTTTATCCTGTTGGATGAACTGAAAACCGGGCAAAATTCTGTGT
CTGGTCCTAAACATGTTTGTACTTATGAAGAACTTTTCCCAATTTTTTGGGAAAATGTT Score = 1970 (295.6 bits), Expect = 1.7e-81, Sum P(43) = 1.7e-81, Identities = 398/400 (99%), Positives = 398/400 (99%), Strand = Plus / Plus Sequence 3. (SEQ ID No.3): subclone BAC22, T7 primer:
GCCTGAGCATCGGTGACAGACATCTTGGTTCCGGGACTCCACCCTGAGTGTTCTGCACAGG
TGAGAGTGTGGAATACAGGG Score = 395 (59.3 bits), Expect = 2.4e-10, Sum P(7) = 2.4e-10, Identities = 79/79 (100%), Positives = 79/79 (100%), Strand = Plus / Plus Sequence 34. (SEQ ID No.4): subclone BAC18, T7 primer :
GTGACTGTTCAAATGCTATGCCTGACTGCTGGTCAATAATGCTCCCTGTCATGATGATAA
TTGGTGACCTTCTGCAAATGTAGACAAGGCACCAACAGTTAGATGTTTCCTTTTATGTGT
TGCCTTGGTCATGATATCTCTTTACACCAATAGAAAAGTAAATAAGATATCTATCTAAGC
TCACATTATATCTTGGAACAGGAAGCACGTCTGTTACCTCTATCCACCTGACCTCATTCC
TCTTAAGACATCTCTAACCTCTAGACATAATTCACTATACACACAGTTCTTCTCTTCTGC
CAAATCTGCTCCTTCAATAACAAACTCAAAAATAACAATGTCCACATGCACAGATCTCCT
CTCAGAAATACCAACAATATGAAAGATGAAGCCAGCATCTTCTCTCCAAAACTTGTAGAA Fig 4 B. Continued

ATGTTTACCAATAAGAACCACATAGATGAACAAAGGAAACAGAATTTAGAAGAGCAATTAT
AA

Score = 2415 (362.3 bits), Expect = 1.4e-101, Sum P(2) = 1.4e-101, Identities = 483/483 (100%), Positives = 483/483 (100%), Strand = Minus / Plus

US 7,666,668 B2

CHROMOSOMAL LOCI FOR THE STRINGENT CONTROL OF GENE ACTIVITIES VIA TRANSCRIPTION ACTIVATION SYSTEMS

This application is a 371 national phase filing of PCT/EP2003/008713 filed Aug. 6, 2003, and claims priority to a U.S. provisional application No. 60/406,344 filed Aug. 28, 2002.

The invention relates to a method for obtaining a chromosomal locus for transgenesis of a multicellular eukaryotic organism, "MEO", to a vector for transgenesis by homologous recombination of a MEO and to the use of such an vector for transgenesis by homologous recombination of a MEO and to the transgenic MEO thus obtainable.

BACKGROUND OF THE INVENTION

The transgenesis of MEO, that can be e.g. a plant or an animal, comprises the integration of a transcription unit into the MEO's genome that comprises a gene and a regulatory sequence that controls the transcription of said gene. To achieve regulation over a maximum amount of orders of magnitude, it is favorable to employ as a regulatory sequence one or more transcription control sequence(s) susceptible for binding transactivators fused to an enhancerless promotor. The basal activity of a chromosomally integrated minimal (i.e. enhancerless) promotor strongly depends on its chromosomal locus. It is well known that the activity of a transcription unit (consisting of at least a promoter, a gene to be expressed and a polyadenylation site), which is inserted into a chromosomal locus either by random or targeted integration, depends strongly on the context of the surrounding chromatin (Palmiter et al. Annu. Rev. Genet. 29, 465-99). When inserted into heterochromatin, transcription units are usually silenced. In euchromatin, on the other hand, the activity of an inserted transcription unit depends on a number of parameters which may affect transcription of the integrated gene positively or negatively. When the transcriptional unit is located close to an enhancer, it will show an increased activity even in the absence of its cognate activator. This problem can be circumvented, if non-homologous recombination is used, by increasing the number of clones (i.e. different integration events) to be screened, or more actively by shielding the transcriptional unit via transcriptional silencers which may be susceptible to control by ligands. However, it is obvious that the first solution of the problem apart from being time consuming leads to the binding of personal and financial resources. The latter solution of the problem is complicated and often reduces the maximum level of transcription of the gene that can be achieved. Furthermore, also the maximum level of transcription of the gene that can be achieved also varies with the chromosomal locus of integration. The locus may also give rise to position effect variegation ("PEV", Palmiter et al. Annu. Rev. Genet. 29, 465-99) and thus, to mosaic expression of the transgene.

SUMMARY OF THE INVENTION

The technical problem underlying the present invention is therefore to provide a method for obtaining a chromosomal locus for transgenesis of a MEO that does not influence or hamper the regulation of the transcription units when introduced into the genome by transgenesis, and that allows the expression of the transgene that forms part of the transcription unit at high levels and that does not give rise to any PEV in respect to the transgene.

In particular, the invention refers to a method for obtaining a chromosomal locus for transgenesis of a first multicellular eukaryotic organism ("first MEO") by homologous recombination or random integration of a DNA sequence comprising DNA being characteristic for the locus, the locus ensuring both the efficient transcription of the gene that is introduced into the genome at said locus (the "transgene"), and the transcriptional control of said transgene by a transactivator without disturbing interference with other transcription control elements, comprising the steps of:

(a) providing a transgenic line of a second multicellular eukaryotic organism ("second MEO"), comprising:
  (a0) a first and a second transcription unit being integrated into the genome of the second MEO;
  (a1) at least the first transcription unit being stably transmitted to the progeny;
  (a2) the first transcription unit comprising one or more reporter genes and one or more transcription control sequence(s), the transcription of the reporter genes being susceptible to control by the binding of a transactivator to the transcription control sequence(s) ("first ligand");
  (a3) the second transcription unit comprising a gene encoding the transactivator;
  (a4) the transactivator's affinity for the transcription control sequence(s) being susceptible to control by the binding of a second ligand; and
  (a5) the transcription of the reporter genes of a cell of the second MEO being susceptible to be stimulated in dependence on the concentration of the second ligand, provided that the transactivator is expressed in said cell;
(b) identifying a transgenic line of step (a) further comprising the following features:
  (b1) the ratio of the amount of the reporter gene(s) product present in a cell in the ON state in which transcription of the reporter gene(s) is maximally stimulated to the amount present in the OFF state in which transcription of the reporter gene(s) is minimally stimulated, is at least $10^2$;
  (b2) no significant amount of any reporter gene product can be detected during a phase comprising development to adulthood if the second MEO is kept in the OFF state during said phase; and
  (b3) no position effect variegation can be observed in respect to the reporter gene(s) in substantially all cells in which the transactivator is expressed.

DETAILED DESCRIPTION OF THE INVENTION

The method usually starts with the preparation of a plurality of transgenic MEO by non-homologous recombination also known as random integration of the trancription unit into the genome of a second MEO used for identification of the locus. The second MEO is preferably a mouse. It is possible to ensure that all transgenic lines obtained by transgenesis exhibit features (a0) to (a5).

The feature (a2) refers to the first transcription unit that is to be introduced into the genome. The first transcription unit comprises one or more reporter genes and one or more transcription control sequence(s), the transcription of the reporter genes being susceptible to control by the binding of a transactivator to the transcription control sequence(s) (also named 'first ligand' hereinafter). A transactivator is a protein that binds to cognate DNA sequences within a promotor and activates the transcription of this promotor. The affinity of the transactivator for the transcription control sequences are dependent on the concentration of a second ligand (e.g. doxycycline). The binding of the transactivator to both ligands shows positive or negative cooperativity. This means in the context of the invention that the binding of the first ligand positively or negatively influences the binding of the second ligand, and vice versa, depending on the nature of the transactivator. The transcription control sequence or the transcription control sequences are preferably built by a tetO sequence that may be multimerized to form e.g. a heptamer of tetO sequences. The use of the $P_{tet}$bi-1 promotor is most preferred (see "Tetracyclines in Biology Chemistry and Medicine" ed. By M. Nelson, W. Hillen and R. A. Greenwald, Birkhäuser Verlag Switzerland (2001), p. 139 et seq. and references therein). The reporter genes are preferably genes encoding a luciferase and/or a recombinase like cre recombinase.

The second transcription unit may be introduced into the genome of the transgenic line of the second MEO by breeding with a transgenic MEO line expressing a transactivator in substantially all cells of the MEO or in a subset of cells that can be histologically identified. This means that the transgenic line of the second MEO of feature (a) will be generally heterozygous in respect to both transcription units. The transactivator encoded by the gene which forms a part of the second transcription unit is preferably selected from a group consisting of tTA and rtTA and derivatives thereof binding to the tetO sequence as a first ligand and to doxycycline as a second ligand with either negative or positive cooperativity. For the transactivators which can be preferably used see "Tetracyclines in Biology Chemistry and Medicine" ed. By M. Nelson, W. Hillen and R. A. Greenwald, Birkhäuser Veriag Switzerland (2001), p. 139 ff. and references therein; PNAS 89:5547-5551 (1992); Annu. Rev. Genet. 36:153-173 (2002).

After providing a plurality of transgenic MEOs each individual is tested for the following features (b1) to (b3):
- (b1) the ratio of the amount of the reporter gene(s) product present in a cell in the ON state in which transcription of the reporter gene(s) is maximally stimulated to the amount present in the OFF state in which transcription of the reporter gene(s) is minimally stimulated is at least $10^2$;
- (b2) no significant amounts of any reporter gene product can be detected during a phase comprising development to adulthood, if the second MEO is kept in the OFF state during said phase; and
- (b3) no position effect variegation, PEV can be observed in respect to the reporter gene(s) in all cells in which the transactivator is expressed.

In feature (b1) the ability of the reporter genes to be regulated is defined. A ratio of the reporter gene present in a cell in the ON state in which transcription of the reporter gene(s) is maximally stimulated to the amount present in the OFF state in which transcription of the reporter gene(s) is minimally stimulated of $10^2$ will ensure that the cross talk of other factors that elevate the transcription background in the OFF state due to enhancers in the vicinity of the integration site of the first transcription unit is limited. However, preferably the ratio is at least $10^4$-$10^5$, more preferably about $10^5$ or even higher. It is clear that the ratio can only be determined for the cells of the second MEO expressing the reporter genes whose expression level is to be tested. This requires that the transctivator is expressed in these cells, too. The expression pattern of the transactivator can be influenced by the choice of the promotor governing the transcription of the gene encoding for the transactivator which forms a part of the second transcription unit.

The OFF and the ON state can be selected by adjusting the concentration of the second ligand in the cells. If the transactivator is tTA or rtTA and the second ligand is a tetracyline, e.g. doxycycline, then the concentration of said ligand can be adjusted by offering a liquid nutrient containing the second ligand to the MEOs, preferably being mice. If one of the reporter genes is luciferase the amount of protein can be detected by conventional testing of the enzymatic activity of the protein homogenate of the tested cells. If one of the reporter genes is cre recombinase the amount of protein can be detected by using R26R transgenic mice as starting material for the production of transgenic mice that have a loxP-flanked DNA insert integrated into their genome that allows simple testing of recombination events as described in the examples.

If the first transcription unit comprises more than one reporter gene all of the reporter genes are preferably coregulated.

In feature (b2) the ability of the reporter genes is defined to be kept silent during a phase comprising development to adulthood including embryogenesis. The regulation of the reporter genes inserted into the genome at a specific chromosomal locus should not vary during development of the MEO. Especially it is important to select for transgenic MEO that do not show significant amounts of any reporter gene during a phase comprising the development to adulthood of the MEO if held in the OFF state. An amount of a reporter gene product is not significant if the amount is not significantly elevated compared to amounts of individuals of the same genotype in the OFF state in any developmental stage. More precisely, the amount of a reporter gene product is not significant if it is 10-fold or less above the detection level of individuals with a null genotype. If a reporter gene is a recombinase (e.g. cre recombinase) the amounts of the reporter gene in the cells of the second MEO are not significant if no recombination activity in the cells is observed during said phase. If the MEO is a mouse the recombination activity is preferably tested using the mouse line R26R. R26R can be used as starting material for the construction of the mouse line trangenic in respect to the first transcription unit or the loxP-flanked gene can be introduced into the genome by breeding.

Feature (b3) prescribes that no position effect variegation, PEV can be observed in respect to the reporter gene(s) in all cells in which the transactivator is expressed and in which therefore the reporter genes can be transcribed and expressed. Generally PEV is presumed to be caused by plasticity of the promotor structure in the surrounding of a transcription unit. This plasticity may result in mosaic expression in populations of identical cells.

In step (c) sequence information of a sequence flanking the first transcription unit is obtained that is sufficient to determine the chromosomal locus on the genome of said second MEO. Preferably step (c) further comprises the following steps:
- (c1) cloning of genome fragments of the second, MEO in, bacterial artificial chromosomes ("BACs") or yeast artificial chromosomes ("YACs");
- (c2) testing the clones of step (c1) for the presence of the first transcription unit; and
- (c3) obtaining sequence information of one or both sequence regions that flank the sequence of the first transcription unit in clones tested positive in step (c2) sufficient to determine the chromosomal locus on the genome of said second MEO.

Cloning of genome fragments in bacterial or yeast artificial chromosomes is known to a person skilled in the art (see examples for references). If an artificial chromosome is tested positive for the presence of the first transcription unit then the flanking sequences are determined until sufficient information is gained to determine the chromosomal locus of the first transcription unit of the respective transgenic line.

The invention further relates to a vector for transgenesis of a multicellular eukaryotic organism ("first MEO") by homologous recombination, the vector comprising at least one transcription unit comprising the gene to be introduced into the genome and sequences flanking the transcription unit(s), characterized in that the flanking sequences are selected so that homologous recombination at a chromosomal locus obtainable by an above method is ensured. Such a vector can also be used for somatic gene therapy.

The invention further relates to a vector for transgenesis of multicellular eukaryotic organism ("first MEO") by random integration of a DNA sequence comprising DNA being characteristic for a chromosomal locus, the vector comprising at least one transcription unit containing the gene to be introduced into the genome (the "transgene") and sequences flanking the transcription unit(s), characterized in that the flanking sequences comprise a sequence being characteristic for a chromosomal locus obtainable by an above method. This vector is also useful for the transgenesis of species for which no ES technology is available. Such a vector can also be used for somatic gene therapy.

The sequences flanking the transcription unit(s) of this vector will generally be much larger than the flanking sequences necessary for ensuring homologous recombination. The length of the flanking sequences is selected so that even if the transgenesis is not effected by homologous recombination but by random integration the transcription of the transgene is regulated as it would be if transgenesis was effected by homologous recombination. That means that the flanking sequences are large enough to emulate the influence of the chromosomal locus obtainable by an above method on the transcription of the transgene. The flanking sequences will have for example a length of 5 kbp to 150 kbp.

If a chromosomal locus is identified, sequence information can be obtained that allows the design of the sequences that flank the transcription unit to be introduced into the genome so that homologous recombination at a chromosomal locus obtainable by an above method is ensured or that allow random integration as described above. The insertion of the transcription unit at the chromosomal locus on the genome of the MEO has the consequence that the regulation of said transcription unit is not hampered by enhancers or other sequences in the vicinity of the integration site, that the transcription up to high levels is possible provided that the transcription unit contains a suitable gene the transcription of which is controlled by a suitable promotor, and that no PEV is observed in respect to the genes of said transcription unit.

A preferred embodiment of such a vector is characterized in that the vector comprises a first and a second transcription unit as defined above spaced by a sequence of sufficient length to prevent any influence of transcription factors that bind to one of the transcription units and the transcription of the respective other transcription unit. Such a vector allows the generation of a transgenic MEO line into which reporter genes encoding e.g. luciferase and/or cre recombinase or any other genes of interest and the transactivator gene encoding the transcativator that controls the transcription of the reporter gene(s) are introduced by one step. If the vector comprises more than one transcription units the transcription units define a cassette that is flanked by sequences being characteristic for a chromosomal locus obtainable by an above method so that homologous recombination at a chromosomal locus obtainable by an above method is ensured if homologous recombination is chosen.

The invention further refers to a method of manufacture a transgenic non-human multicellular eukaryotic organism by transgenesis via homologous recombination or random integration using a vector as described above.

Figure 1:
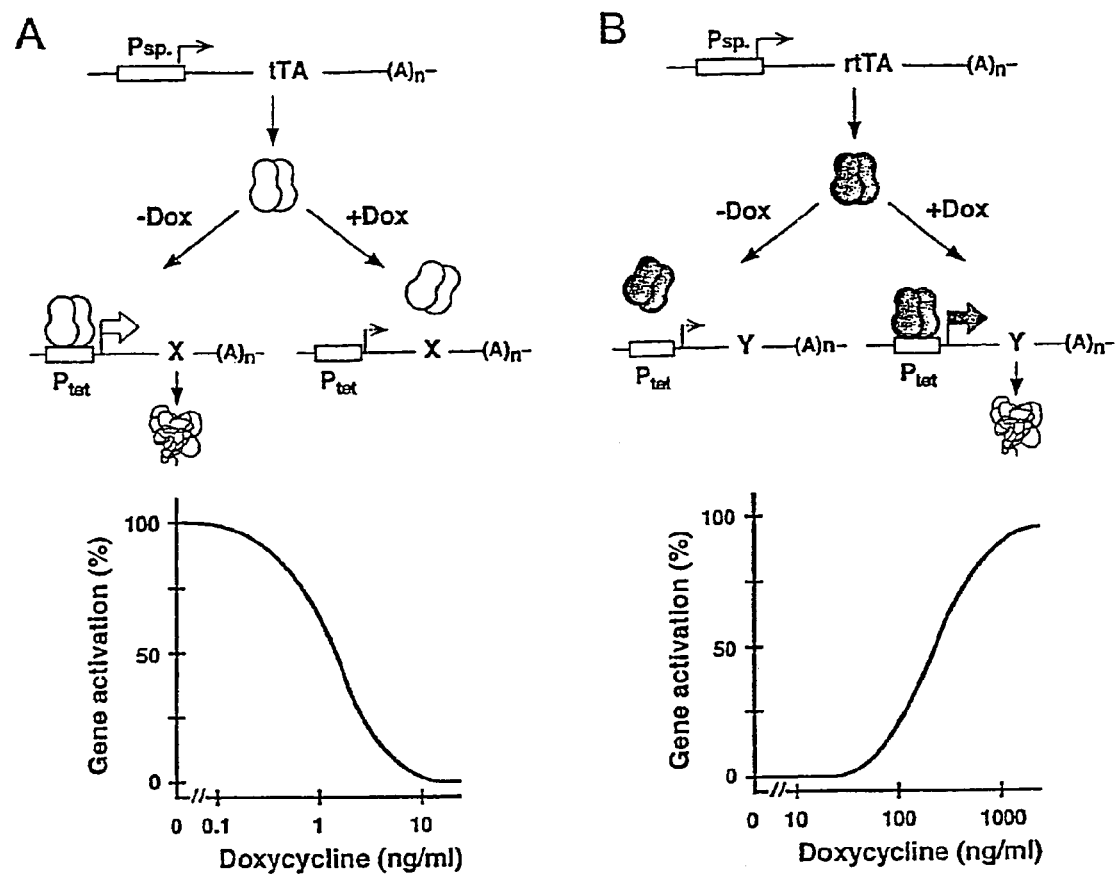

The figures show:

FIG. 1: Outline of the Tet regulatory principle. Left upper part shows the mode of action of the Tc controlled transactivator (tTA). tTA binds in absence of the effector molecule Dox to the tetO sequence within $P_{tet}$ and activates transcription of gene x. Addition of Dox prevents tTA from binding and, thus, the initiation of transcription. Left lower part depicts the dose response of Dox on tTA dependent gene expression. Gene activity is maximal in the absence of the antibiotic but as effector concentrations increase transcription gradually decreases to background levels at Dox concentration>5 ng/ml. Right upper part illustrates the mechanism of action of the reverse Tc controlled transactivator (rtTA). rtTA is identical to tTA with the exception of 4 amino acid substitutions in the TetR moiety. rtTA requires Dox for binding to tetO sequences within $P_{tet}$ in order to activate transcription of gene y. Right lower part outlines the dose response of Dox on the rtTA dependent transcription activation. By increasing the effector concentration beyond 20 ng/ml of Dox, rtTA dependent gene expression is gradually stimulated. $P_{tet}$ is a minimal promoter fused downstream of an array of 7 tet operators (7). It interacts with tTA as well as with rtTA.

Figure 2:
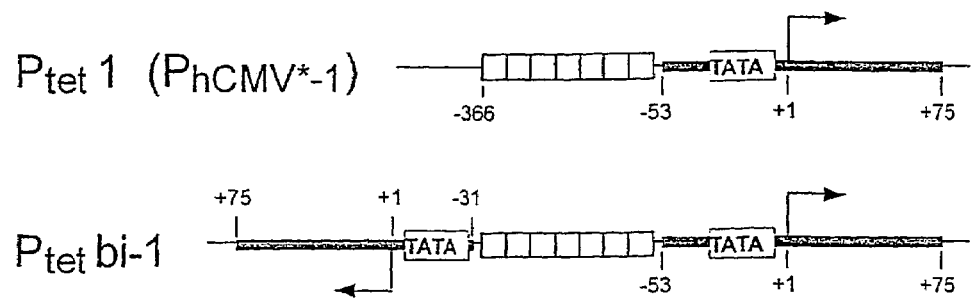

FIG. 2: Topography of tTA/rtTA responsive promoters ($P_{tet}$). $P_{tet}$-1 is composed of a minimal promoter derived from the human cytomegalovirus promoter IE of which the sequence between −53 and +75 (+1 being the transcriptional start site) was fused to an array of 7 equally spaced tet operator sequences (5). In $P_{tet}$bi-1, two minimal promoters flank either side of the array of tet operators as described in ref. 9.

Figure 3:
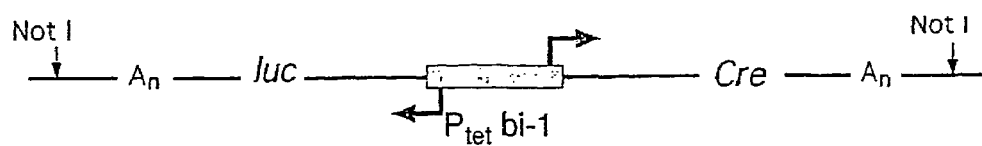
Figure 3:
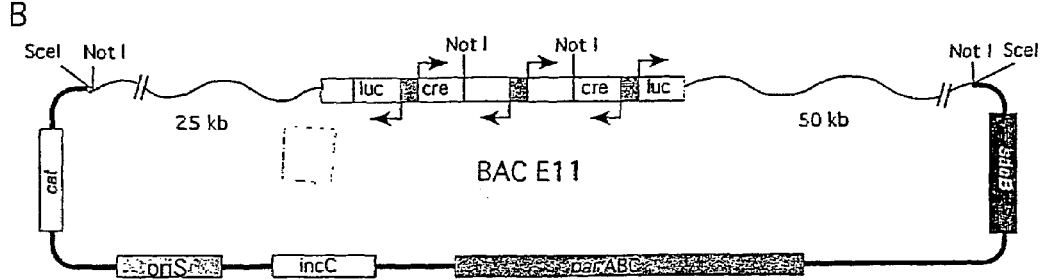

FIG. 3: Structure of the bidirectional luc/cre transcription unit and of BAC E11. A. The genes of the firefly luciferase and of Cre recombinase, respectively, are coregulated by $P_{tet}$bi-1. The luc gene is flanked by a SV40, the cre gene by the human growth hormone (hGH) polyadenylation site ($A_n$). The expression cassette can be retrieved via unique NotI cleavage sites indicated. B. BAC E11 contains three tandemly integrated luc/cre transcription units and at the left border a fragment of the hGH polyA site. The insert is flanked at the left side by a 25 kb and at the right side by a 50 kb fragment of mouse DNA. Sequence analysis revealed that the two regions stem from mouse chromosome 6. The size of the insert in BAC E11 is 95 kb, it is flanked by NotI sites as indicated. The cloning vehicle pBeloBAC-HD has been described previously (10).

FIG. 4: Localization of the E11 region in C1 of mouse chromosome 6. A. Partial sequences of the E11 insert were obtained by probing respective E11 DNA with primers initiating DNA synthesis from sequences within the vector pBeloBAC (primer 3) or pBluescript (T7 sequencing primer), respectively. B. Blast results of the 4 sequences shown using the ENSEMBL mouse genomic library (www.ensembl.org) C. Position of the E11 region within C1 of mouse chromosome 6.

Figure 5:
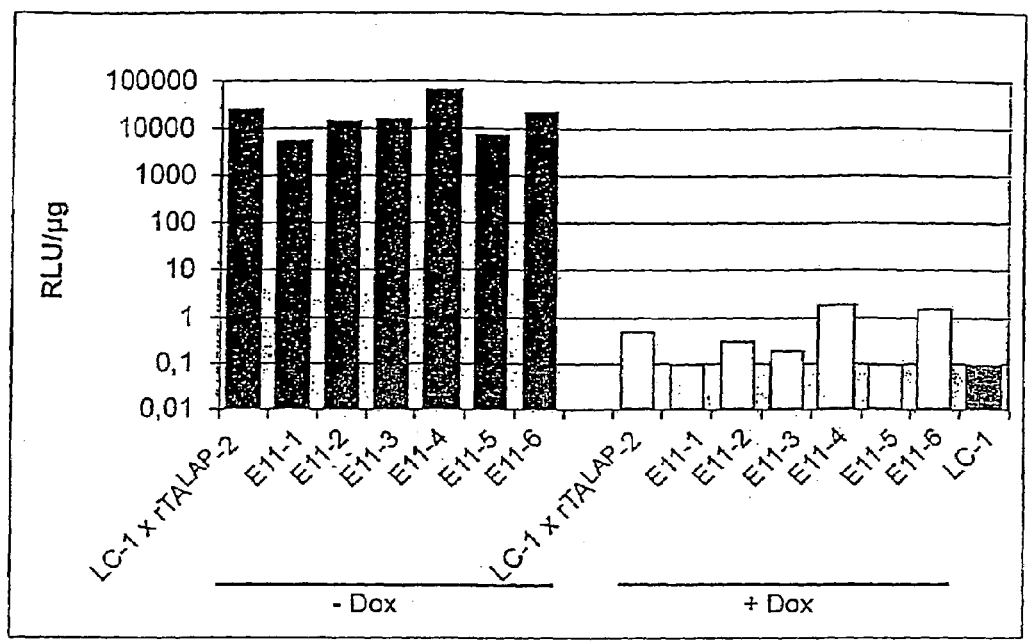

FIG. 5: Analysis of E11 transgenic mice. Six mouse lines, E11-1 to E11-6, stably transmitting the intact E11 fragment were crossed with mice of the $TA^{LAP}$-2 line expressing tTA specifically in hepatocytes. Luciferase activity in presence and absence of Dox was determined in extracts of the liver and various other tissues and then compared with respective values obtained with the parent LC-1 mouse line. Luciferase activity measured in liver extracts is shown. The values given are the means from 4 to 5 animals.

Figure 6:
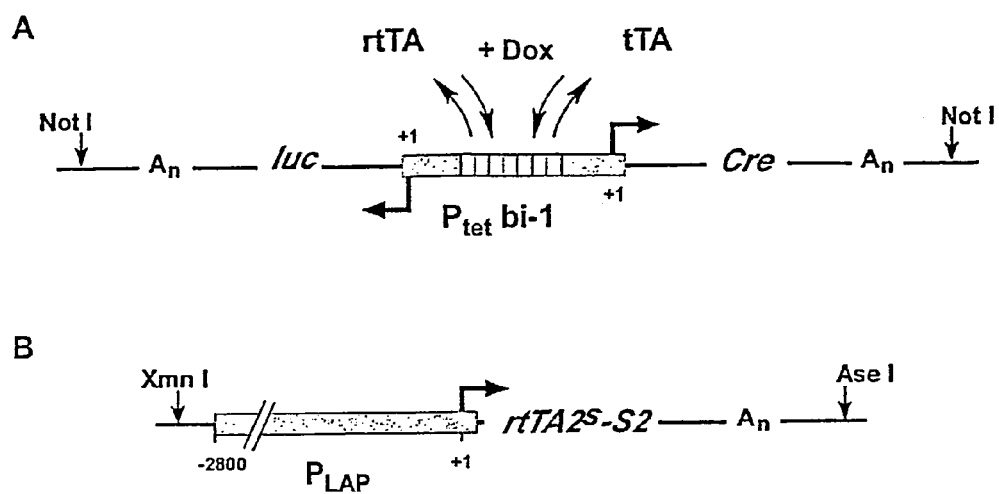

FIG. 6: Transcription units incorporated in the LC-1 and rTA$^{LAP}$-1 mouse line, respectively. (A) The bidirectional tTA/rTA responsive promoter P$_{tet}$bi-1, present in LC-1 animals, contains an array of seven tet operator sequences flanked by two minimal promoters derived from the human cytomegalovirus promoter IE. The two polyadenylation sites are derived from the human growth hormon (cre) and the SV40 early transcription unit (luc), respectively. The promoter is activated by rtTA in presence and by tTA in absence of Dox. (B) Animals of the rTA$^{LAP}$-1 mouse line contain a transcription unit consisting of the LAP promoter region which extends to −2800, a synthetic gene encoding the rtTA2$^S$-S2 transactivator variant, followed by the SV40 polyadenylation site. Transcriptional start sites are denoted as +1.

Figure 7:
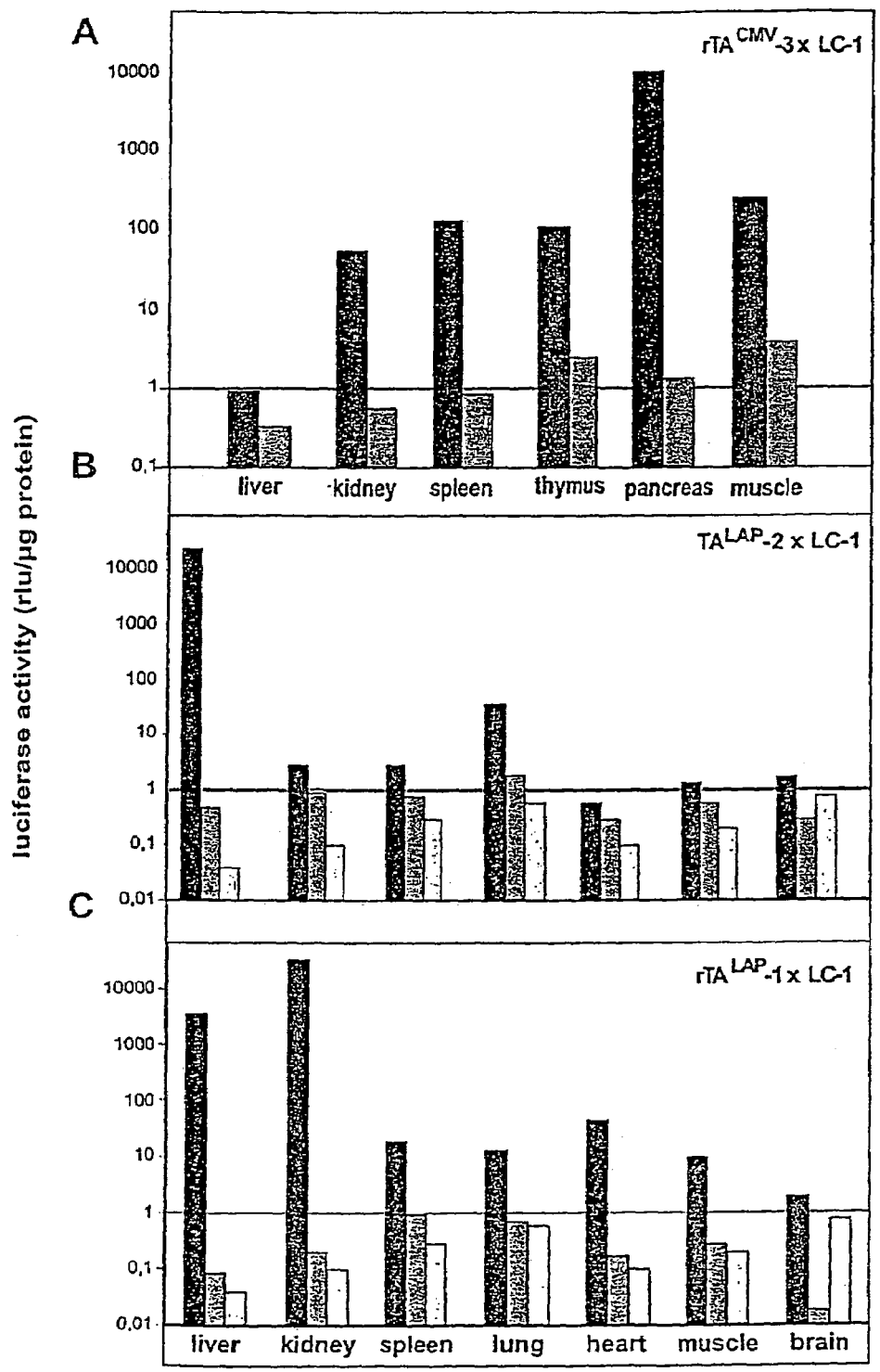

FIG. 7: Luciferase activity in various organs of LC-1 animals in the induced and uninduced state. LC-1 animals were crossed with individuals expressing rtTA or tTA in various cell types/tissues. Luciferase was measured in extracts of tissues indicated. (A) rTA$^{CMV}$-3/LC-1, (B) TA$^{LAP}$-2/LC-1 and (C) rTA$^{LAP}$-1/LC-1 were analyzed. Induced and uninduced levels of luciferase are depicted as dark and intermediate grey columns. The light grey columns in B and C show luciferase activity in single transgenic LC-1 mice. The instrumental luciferase background around 1 rlu/μg of protein is indicated. The luciferase values given are the means of 4 to 6 animals.

Figure 8:
Figure 8:
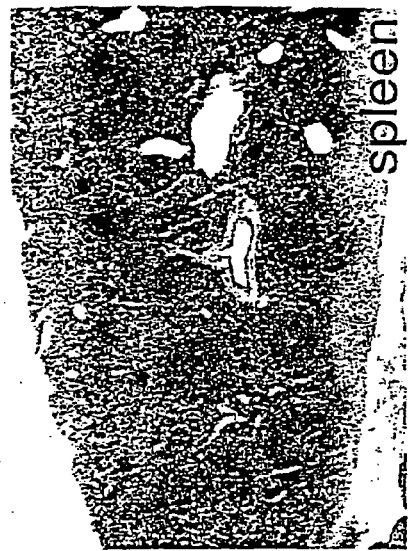
Figure 8:
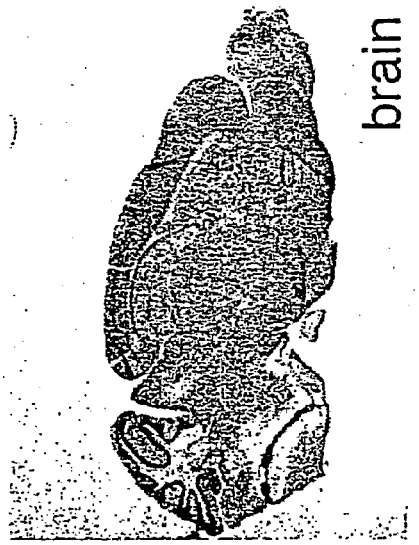
Figure 8:
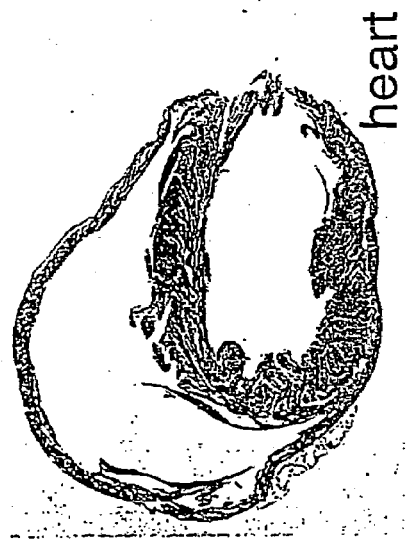
Figure 8:
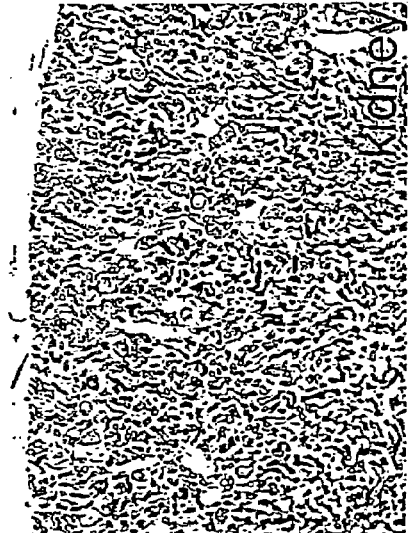
Figure 8:
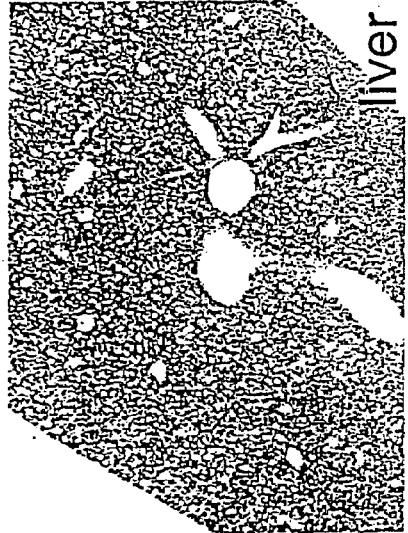

FIG. 8: Examination of LC-1/R26R double transgenic animals for CRE activity. Histological specimen of 14-month-old animals are shown. Samples were stained with Xgal overnight and counterstained with nuclear fast red. No b-gal actvity could be detected in any organ/tissue examined of which 6 are exemplified here.

Figure 9:
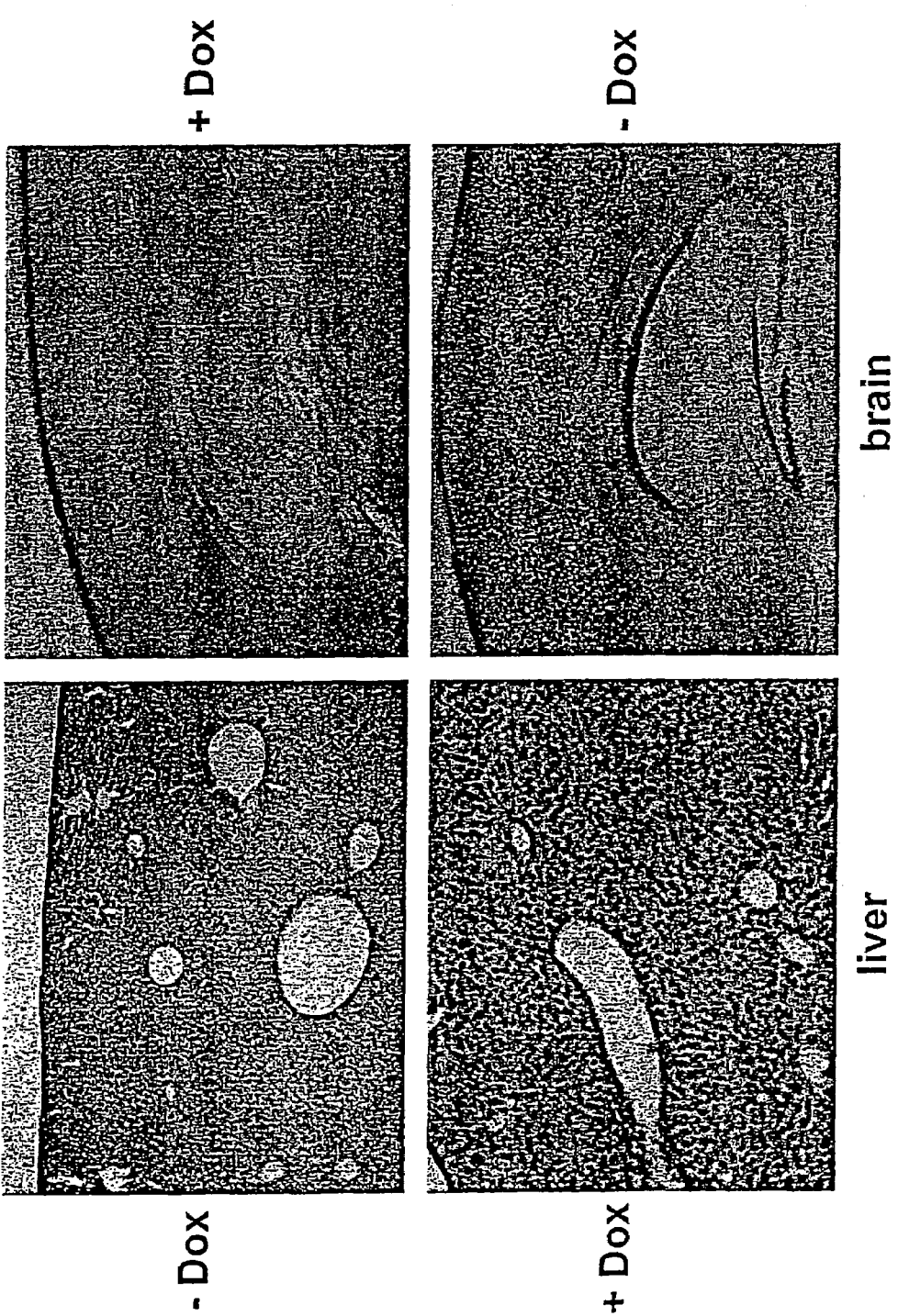

FIG. 9: Induction of CRE recombinase in rTA$^{LAP}$-1/LC-1/R26R animals. CRE (and luciferase) synthesis was induced in triple transgenic animals by i.p. injection of Dox. Histological analysis of CRE activity via Xgal staining revealed a remarkably specific pattern which reflects the activity of the LAP promoter in the rTA$^{LAP}$-1 mouse line. Staining as in FIG. 8.

Figure 10:
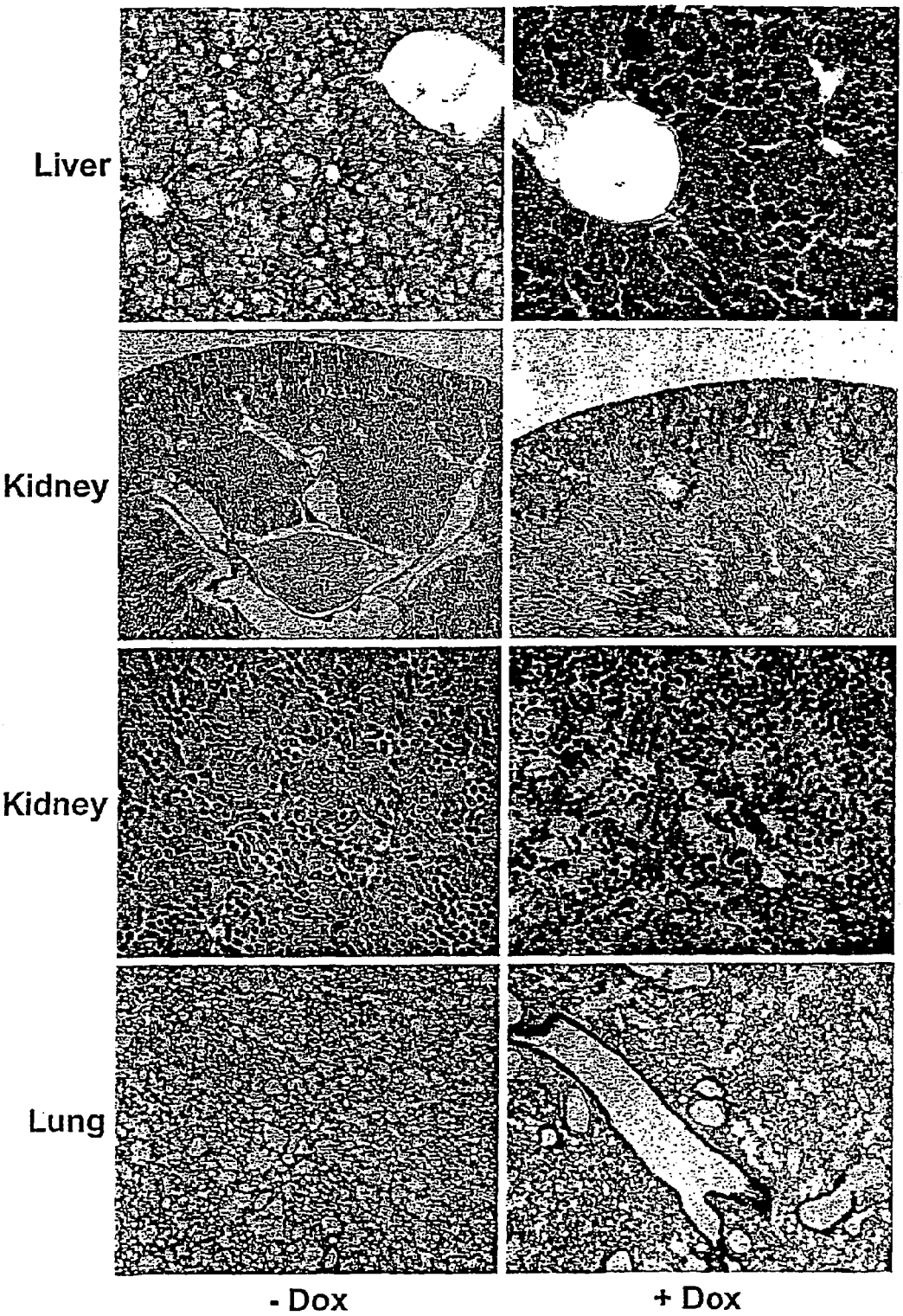

FIG. 10: Identification of CRE recombinase by immunostaining. LC-1 animals crossed with either rTA$^{LAP}$-1 or TA$^{CamK}$-1 mice were induced by Dox addition or withdrawal, respectively. No sign of CRE protein was detected in the uninduced state, whereas intense staining is observed upon induction in hepatocytes and neurons depending on the expression pattern of the transactivators in the respective mouse lines.

The invention is further illustrated by the following examples, which are not to be understood as limiting the scope of the claimed subject matter.

EXAMPLE 1

Introduction

The tetracycline (Tc) controlled gene expression systems (Tet systems) have developed into widely applicable tools for the study of gene function in vivo (1,2). Particularly in the mouse, presently the prime model of mammalian genetics thanks to transgenesis and embryonic stem cell technology, the principle of conditional gene activation as provided by the Tet systems allows to dissect gene functions in vivo with unprecedented precision. Indeed, exploiting the Tet systems in vivo is increasingly yielding new insights into such fundamental processes as development, behaviour and disease (3, 4, 5, 6). Thus, the Tet systems have considerable impact not only on basic research in biology, but also on applied aspects of life sciences including but not limited to development of cell lines for high throughput screening and fermentation
    novel animal models for human diseases
    gene therapy
    sterile insect control
    plant breeding, etc.

The principle of Tc controlled gene expression is depicted in FIG. 1. Two complementary systems have been developed (7, 8). In both systems, a gene of interest is placed under the control of P$_{tet}$, a promoter responsive for Tc controlled transcription activators (tTA or rtTA). The binding of the transactivators to P$_{tet}$-1 and thus transcription activation depends on the presence or absence of doxycycline. (Dox), the Tc derivative most commonly. used for Tet regulation in vitro and in vivo.

A hallmark of a properly set up Tet regulation in any cell or organism is the tightness of control and the wide range of regulation which may reach 5 to 6 orders of magnitude.

Importantly, Tet regulation permits not only the repeated activation and inactivation of a gene under study, it also enables the researcher to tune the expression of a gene to a defined level by administering the appropriate amount of the inducer Dox (FIG. 1). This latter feature is of particular interest as it allows to induce graded perturbations into a cell/organism.

The potential to reverse induced perturbations and the quantitative control of the activity of a gene of interest have made the Tet technology the by far most widely applied gene control system (2, 5).

To achieve optimal Tet regulation, several conditions have to be fulfilled. The invention described herein refers to the most crucial one: the properties of the chromosomal loci harbouring P$_{tet}$ controlled transcription units containing the gene(s) of interest. Ideally, such loci do not influence P$_{tet}$ in its inactive state while allowing its high activation by tTA/rtTA. Such loci we have termed "silent but activatable" (s/a).

Here, the identification, isolation and characterization of a chromosomal region of a transgenic mouse are described, which fulfills the conditions of a s/a locus. This locus, designated LC-1, that harbours both the luciferase and the Cre recombinase gene under P$_{tet}$bi-1(9; FIG. 2) control, can be transferred via transgenesis to náive mice. In the resulting transgenic animals, the P$_{tet}$ controlled transcription units can be regulated tightly and over a wide range as in the parent animals from which the LC-1 locus was physically retrieved. Thus, the LC-1 locus allows the generation of transgenic animals with predictable Tet regulation properties.

BACKGROUND

It is well known that the activity of a transcription unit (consisting of a promoter, a gene to be expressed and a polyadenylation site), which is inserted into a chromosomal locus either by random or targeted integration, depends strongly on the context of the surrounding chromatin (11). When inserted into heterochromatin, transcription units are usually silenced. In euchromatin, on the other hand, the activity of an inserted transcription unit depends on a number of parameters which may affect transcription of the integrated gene positively or negatively. The locus may also give rise to position effect variegation (PEV, 11) and thus to mosaic expression of the transgene.

In a typical Tc controlled transcription unit, P$_{tet}$ governs the expression of a gene of interest (FIG. 1). P$_{tet}$ consists of an array of tet operators fused upstream of a minimal RNA polymerase II promoter (FIG. 2). Ideally, a minimal promoter exhibits no activity on its own when transferred to a cell. Therefore, when fused to tet operators, its activity will exclusively depend on tTA/rtTA an Dox.

When a $P_{tet}$ controlled transcription unit is inserted into the genome of a cell, its function will strongly depend on the properties of the integration site (7, 11). How a chromatin landscape affects an ectopically inserted transcription unit is not understood and, thus, not predictable. The surrounding of the integration site may induce a background activity of $P_{tet}$ via nearby transcriptional enhancers which can act over a distance. The locus will, however, also determine the level of induction which can be achieved (7, 13). Using the approach of random insertion as it is common in the generation of cell lines and transgenic mice, the vast majority of insertions will occur in sites not optimal for tight and broad range regulation via the Tet systems (1, 7). Whereas at the level of cells in culture clones with satisfying regulation potential can be readily identified by efficient screening or selection procedures, the identification of respective mouse lines is extremely time consuming and costly as only 5 to 10% of the founder animals are expected to exhibit the desired properties.

The advent of the yeast (YAC) and bacterial (BAC) artificial chromosome technology (14, 15) where genomic fragments of 50 to 400 kb can be physically isolated, has opened up new possibilities for transferring chromosomal loci, which due to their size would allow to also transmit properties specific for a respective locus (16). We have made use of this technology and generated a BAC containing the functionally defined locus identified in our LC-1 mouse line for transfer of locus specific properties in mice.

Identification and Characterization of the LC-1 Locus

The LC-1 mouse line characterized herein (17) contains the luciferase (luc) and the CRE recombinase (cre) gene under the control of $P_{tet}$bi-1 (FIG. 2, 3). In this mouse line, the bidirectional transcription unit appeared integrated in a chromosomal site that fulfills our definition of a s/a locus:

In none of the tissues examined, there is luciferase activity detectable (17).
When crossed with tTA or rtTA expressing mouse lines luciferase can be induced to high levels in the ON state and repressed to background levels in the OFF state in respective tissues (17).
luc and cre are coregulated (18).
Efficient deletion of loxP flanked DNA is observed upon Cre/luciferase induction whereas no recombination throughout the animal is seen in the non-induced state (17).
In all cells examined, namely hepatocytes, T cells and neurons of the hippocampus, position effect variegation has not been observed.

The LG-1 locus, thus, exhibits all the properties of a s/a locus in all cell types examined. It, therefore, appeared to be a good candidate for generating a vector system for establishing Tet regulatable transgenic mice with predictable properties.

Isolation of the LC-1 Locus via the BAC Technology

Using DNA of the LC-1 mouse line, a BAC library was established using the plasmid pBeloBAC-HD (10) and *E. coli* strain DH10B™. Bacterial clones containing pBeloBAC-HD with large inserts of mouse DNA were selected via sacB inactivation (10). Clones containing the LC-1 insert were identified via a PCR based HTP screening procedure. Of several positive colonies BAC E11 containing a 95 kb fragment was further studied. The 95 kb fragment was analyzed by subcloning and partial sequence determination. FIG. 3 depicts the results of this analysis: The bidirectional transcription unit controlled by $P_{tet}$bi-1 is inserted 3 times in tandem in a region of chromosome 6 of the mouse (FIG. 4) which, according to the sequence comparisons (data libraries of Celera and ENSEBL), appears not to contain any open reading frames of sensible size. The insert is rather centrally located within the 95 kb fragment of BAC E11. The sequences flanking the LC-1 insert suggest that, unexpectedly, no major rearrangements have occurred in the genomic DNA during the integration event. The chromosomal site identified by the LC-1 insertion may, therefore, also be suitable for direct targeting with $P_{tet}$ controlled transcription units via homologous recombination in ES cells.

Transfer of BAC E11 into Naive Mice

The 95 kb fragment spanning the LC-1 locus was isolated from BAC E11 via ScdI cleavage and pulse field electrophoresis, before it was injected into the pronucleus of fertilized oocytes of Bl6/DBA mice. Of 10 DNA positive founders, nine transmitted the transgene of which eight showed tight and broad range regulation of luciferase in primary fibroblast cultures (13) derived from ear biopsies of the animals. Analysis of the inserted DNA in these founders via PCR revealed that six founders had internalized the intact 95 kb fragment. These founders were used to establish the E11 mouse lines E11-1 to E11-6 (FIG. 5).

High Fidelity Transfer of LC-1 Regulation Characteristics

Animals of the six E11 mouse lines were crossed with individuals of the $TA^{LAP}$-2 line. The latter line expresses the tTA encoding gene exclusively in hepatocytes (13). Accordingly, Dox controllable expression is expected only in the liver of double transgenic animals. Groups of 4 to 6 $TA^{LAP}$-2/E11 animals were supplied with either Dox containing (2 mg/ml) or plain drinking water for two weeks before they were sacrificed and extracts of various tissues subjected to luciferase activity measurements. All E11 mouse lines exhibited luciferase expression patterns which closely resembled the one of the parent LC-1 mouse line: luciferase activity was virtually absent in all tissues, independent of Dox supply, except for the liver. In liver extracts, high luciferase levels are monitored in absence and background values in presence of Dox, as shown in FIG. 5. There is just the E11-4 line which apparently can be induced around 3 times higher in hepatocytes as compared to the parent (LC-1) mouse line. This line exhibits also a somewhat elevated background activity. We do not know yet whether this mouse line may have multiple insertions of the 95 kb fragment. The results show that indeed the 95 kb fragment of mouse chromosome 6 as identified herein is capable of transferring with high fidelity the very favorable regulation properties of the LC-1 mouse line to other individuals by simple DNA transfer.

Advantages of the LC-1 Technology

Experimental animals and other organisms, in which a gene of interest can be expressed at will, controlled from outside, are of great value for the study of gene functions and the modelling of diseases. In mammals, particularly in the mouse, this strategy has yielded numerous new insights during the last 5 to 8 years, whereby for a number of reasons (1, 2, 4, 5), the Tet systems have developed into the most widely applied technology (2). Nevertheless up to date, the generation of mouse lines where a gene of interest can be controlled tightly and over a broad range has been demanding due to the unpredictable influences of the chromosomal site where a $P_{tet}$ controlled transcription unit is integrated.

With the LC-1/E11 locus of chromosome 6 of the mouse, a locus with favorable characteristics for Tet regulation has been identified which can be transferred to other animals with high efficiency and fidelity. Thus, 100% of the transgenic animals which received the intact 95 kb fragment showed regulation properties that closely ressemble the ones of the parent LC-1 mouse line. Two out of three further mouse lines which did not contain the full length fragment still showed excellent regulation characteristics in primary fibroblasts. Thus, 8 out of 9 founder animals exhibit the desired properties of the LC-1 locus. This contrasts with the general success rate for obtaining such animals which lies around 5%. The LC-1/E11 fragment can be used as a vehicle for any $P_{tet}$ controlled expression unit and, thus, make the generation of functional animals predictable. The application of the LC-1/E11 technology will lead to a significant reduction of animals required and of time invested in respective projects and will, thus, greatly lower the costs involved.

The LC-1/E11 locus can obviously be used as vehicle for any gene or expression unit of interest. As other transcription control systems (3) are similarly susceptible to local influences of the chromatin structure, the application of the LC-1/E11 vehicle will be advantageous as well.

Generating Tet Controlled Conditional Mouse Mutants in One Step

Following the most reliable approach for developing Tet controlled conditional mouse mutants, one generates transactivator mouse lines that express tTA or rtTA under the control of a tissue specific promoter of choice. Similarly, a receiving mouse line has to be created which contains the gene of interest under $P_{tet}$ control, taking into account a costly screening procedure for mouse lines where the $P_{tet}$ controlled transcription unit is inserted into a s/a locus. Coinjection of two DNA fragments of which one carries the tTA/rtTA, the other the $P_{tet}$ transcription unit is rarely successful. Since the two DNA species cointegrate with high probability into the same locus, transcriptional enhancers of the promoter driving the tTA or rtTA gene will be placed in close proximity of $P_{tet}$, thus, causing elevated background activities and preventing tight control. This problem is not expected to arise when a DNA fragment carrying a tTA or rtTA gene with its respective promoter cointegrates with a $P_{tet}$ controlled. transcription unit embedded in the 95 kb LC-1/E11 vector, as respective enhancers will be spaced 25 or 50 kb away from $P_{tet}$, generally too far to exert any influence.

Allowing for cointegration, the LC-1/E11 technology will, therefore, decisively simplify the generation of Tet regulatable conditional mouse mutants that may be obtained and characterized within 4 instead of 12 months, as required with the present-day approach.

Finally, the LC-1/E11 fragment may be large enough for taking up a second integration site within the 50 kb flanking region. This site could be used for integration of a transcription unit expressing tTA or rtTA under the control of a tissue specific promoter. For many promoters, a distance of 25 kb will be sufficient to shield $P_{tet}$ from respective enhancer activities. Constructs which contain the entire Tet regulation system and the gene of interest in a functional arrangement would simplify the establishment of conditional mouse mutants even further.

Targeting s/a loci via Homologous Recombination

Sequence analysis of the mouse derived inserts in BAC E11 has shown that the LC-1 transcription units have integrated into a contiguous region of chromosome 6 of the mouse. No functional open reading frames were identified in that region. It, therefore, appears promising to target this locus with transcription units of interest via homologous recombination in ES cells. It will be of particular interest to insert into that region transcription units controlled by tissue specific promoters. It appears likely that these promoters, when inserted in a "neutral" chromatin environment, will maintain their characteristic activity profile.

Generating Tet Controlled Conditional Mutants of the Rat

Considering the high sequence homologies between rat and mouse genes, one can safely assume that numerous genes modified for studies in the mouse will also be applicable in the rat. As the rat has remained the system of choice in many areas of biomedical research, an experimental strategy which permits the efficient generation of conditional mutants with these animals will be of great value.

In absence of an ES cell technology for this animal species, the LC-1/E11 approach, particularly when applied in a one-step procedure as described above, will constitute a major breakthrough. There is little reason for assuming that species differences would prevent the function of the LC-1/E11 locus in rats.

Application of the LC-1/E11 Technology in Other Mammals

It appears likely that loci like the LC-1/E11 will be functional in other mammals, valuable in food productions, gene farming, disease models, etc. In many of these species, the technique of transgenesis is established. Considering, however, the generation time and the costs involved, it is extremely difficult to derive conditional mutants in the traditional way, namely by creating transactivator (tTA/rtTA) and receiving lines (containing $P_{tet}$ controlled gene of interest) which would then allow to obtain double transgenic individuals by breeding. The LC-1/E11 technology will open up new perspectives for the generation of conditional gene expression in these promising but very complex and costly systems. Particularly when both the tTA/rtTA and the $P_{tet}$ controlled expression units are transferred via two separate BAC derived vehicles, a high success rate for tissue specific and tightly controllable mutant lines can be expected. Due to cointegration, the two expression units will not segregate during breeding while the two transcription units will function independent from each other.

Application in Gene Therapy

A predictable and tight regulation is also sought in various regimens of gene therapy. The LC-1/E11 principle may be of value in this important field as well. Preliminary experiments in our laboratory have shown that indeed the LC-1/E11 fragment can lead to well regulatable human cells (HeLa cells) in culture, indicating interesting general properties of the LC-1/E11 locus.

Literature

1. Baron, U. and Bujard, H. (2000) The Tet repressor-based system for regulated gene expression in eukaryotic cells: principles and advances. Methods Enzymol. 327, 659-686.
2. Gossen, M. and Bujard, H. (2001) Tetracyclines in the control of gene expression in eukaryotes. In: Tetracyclines as molecular probes for micro and mammalian biology. eds. M. Nelson, W. Hillen, R. A. Greenwald. p. 139-157, Birkhäuser Verlag, Basel, Switzerland.
3. Lewandoski, M. (2001) Conditional control of gene expression in the mouse. Nat. Rev. Genet. 2, 743-755.
4. Schönig, K. and Bujard, H. (2002) Generating conditional mouse mutants via tetracycline controlled gene expression. In: "The Transgenic Mouse: Methods and Protocols", eds. Jan van Deursen and Marten Hofker, p. 69-104, Humana Press Inc., USA
5. Gossen, M. and Bujard, H. (2002) Studying gene function in eukaryotes by conditional gene inactivation. Annu. Rev. Genet. 36, 153-173.

6. Mansuy, I. and Bujard, H. (2000) Tetracycline-regulated gene expression in the brain. Curr. Op. Neurobiol. 10, 593-596.
7. Gossen, M. and Bujard, H. (1992) Tight control of gene expression in mammalian cells by tetracycline responsive promoters. Proc. Natl. Acad. Sci. USA 89,5547-5551.
8. Gossen, M., Freundlieb, S., Bender, G., Müller, G., Hillen, W. and Bujard, H. (1995) Transcriptional activation by tetracycline in mammalian cells. Science 268, 1766-1769.
9. Baron, U., Freundlieb, S., Gossen, M. and Bujard, H. (1995) Coregulation of two gene activities by tetracycline via a bidirectional promoter. Nucl. Acids Res. 23, 3605-3606.
10. Baldinger, T. (2000) Konstruktion eines BAC-Vektors zur Klonierung großer genomischer DNA-Fragmente. Diploma Thesis, Universität Heidelberg
11. Palmiter, R. D. and Brinster, R. L. (1986) Germ-line transformation of mice. Annu. Rev. Genet. 20, 465-99.
12. Wilson, C., Bellen, H. J. and Gehring, W. J. (1990) Position effects on eukaryotic gene expression. Annu. Rev. Cell Biol. 6, 679-714.
13. Kistner, A., Gossen, M., Zimmermann, F., Jerecic, J., Ullmer, C., Lübbert, H. and Bujard, H. (1996) Doxycycline-mediated, quantitative and tissue-specific control of gene expression in transgenic mice. Proc. Natl. Acad. Sci. USA 93, 10933-10938.
14. Peterson, K. R., Clegg, C. H., Li, Q. and Stamatoyannopoulos, G. (1997) Production of transgenic mice with yeast artificial. chromosomes. Trends Genet. 13, 61-66.
15. Yang, X. W., Model, P. and Heintz, N. (1997) Homologous recombination based modification in *Escherichia coli* and germline transmission in transgenic mice of a bacterial artificial chromosome. Nat Biotechnol. 15, 859-865.
16. Huxley, C. (1998) Exploring gene function: use of yeast artificial chromosome transgenesis, methods: A Companion to Methods in Enzymology 14, 199-210.
17. Schönig, K., Schwenk, F., Rajewsky, K. and Bujard, H. (2002) Stringent doxycycline dependent control of CRE recombinase in vivo. See Example 2
18. Hasan, M. T., Schönig, K., Graewe, W. and Bujard, H. (2001) Longterm, non-invasive imaging of regulated gene expression in living mice. Genesis 29, 116-122.

EXAMPLE 2

Summary

The strategy of modulating gene activities in vivo via CRE/loxP recombination would greatly profit from subjecting the recombination event to an independent and stringent temporal control. Here, a transgenic mouse line, LC-1, is described where the expression of the cre and the luciferase gene is tightly controlled by the Tet system. Using the R26R mouse line as indicator for CRE activity and mouse lines expressing tetracycline controlled transactivators in various tissues, it is shown that (i) in the non-induced state no recombination event is detected throughout development and adulthood of an animal; (ii) upon induction efficient recombination occurs in the adult animal in all tissues where tTA/rtTA is present, including hepatocytes, kidney cells, neurons and T lymphocytes; (iii) no position effect appears to be caused by the LC-1 locus. Moreover, using the novel rTA$^{LAP}$-1 mouse line, it is demostrated that in hepatocytes complete deletion of the loxP-flanked insert in R26R animals is achieved in less than 48 hrs after induction. Thus, the LC1 mouse appears suitable for exploiting two rapidly increasing collections of mouse lines of which one provides tTA/rtTA in specific cell types/tissues, the other a variety of loxP-flanked genes.

Introduction

Site-specific recombinases such as CRE and FLP derived from microorganisms catalyze recombination between their cognate recognition sites, loxP and frt, respectively, with high specificity. Both systems function in mammalian cells and particularly the CRE/loxP system has developed into a powerful tool for the in vivo manipulation of genomes in transgenic mice (for review see ref. 1, 2, 3). While the recombinases permit to invert or delete DNA fragments in cis or switch segments of DNA in trans and thus allow a variety of modifications including chromosome engineering, the most common application is the conditional deletion of a DNA fragment flanked e.g. by two loxP sites in order to silence or activate a gene. In the most generally applied approach, conditionality of recombination is based on the specificity of the promoter driving the expression of the cre gene and, accordingly, recombination will occur in dependence of the spatial and temporal activity of the respective promoter. Not withstanding its great potential, this approach has a number of limitations. Thus, the activity spectrum of a promoter depends on a rigid developmental/differentiation program of an organism and, accordingly, as recombination induces irreversible alterations, the final pattern of CRE action will reflect the "history" of a promoter's activity throughout development. While such a cumulative recombination pattern may be of interest in some studies, it diminishes the precision of the approach in others. Moreover, as CRE will act whenever a respective promoter becomes active in a particular tissue/cell type, it will not be possible to induce recombination at a later time in the lifespan of an animal, thus preventing a thorough study of the unperturbed state in the same individual. Finally, there is increasing evidence that by recognizing pseudo loxP sites within the mouse genome CRE can cause undesired recombination events (4, 5). Even if such recombinations occur at a low rate, the outcome will depend on the intracellular concentration of CRE and the duration of its expression.

Obviously, controlling CRE activity from outside at will would enhance the scope of the technology significantly as numerous attempts demonstrate. Two approaches have primarily been followed (for review see ref. 2): controlling either the transcription of the cre gene or the activity of CRE itself. Both principles have been applied with some success, but problems concerning the general applicability have remained. They were connected with the inducers of the control systems (interferon, synthetic steroids such as tamoxifen and Ru486), the diminished enzymatic activity of the CRE fusion proteins and the tightness of the control systems over long periods of time. The latter parameter is particularly important in the study of long lived cells as recombination events caused by leakiness of the control system accumulate over time.

When properly set up, the Tet regulatory system allows tight control of transcription (7, 8) and indeed control of CRE via doxycycline (Dox) has been reported (8, 9, 10). The approach of Utomo et al. (9) seems particularly attractive in this context. Here, a single vector encodes two transcription units of which one contains the gene of a tetracycline controlled transactivator (tTA or rtTA) driven by a cell type specific promoter, whereas the other one encodes CRE controlled by the tTA/rtTA responsive promoter $P_{tet}$-1 (7). Mouse lines derived with this vector were shown to control CRE activity satisfactorily in the expected tissues. Nevertheless, like other regulatory systems which function via promoter activation, tightness and range of regulation of the Tet system depend strictly on the genomic locus where the $P_{tet}$ controlled transcription unit is integrated. For example, enhancers which may act over considerable distances can activate the minimal promoter within $P_{tet}$ when located near the integration site. One would, therefore, predict that the Utomo vector will function in some but not in other settings.

Here, it is described an alternative strategy which is based on a mouse line, designated LC-1, that contains a $P_{tet}$-cre transcription unit in an appropriate chromosomal locus and which exhibits remarkable properties: (i) There is no CRE mediated recombination in the uninduced state in any cell during development and during at least 14 months of adulthood; (ii) upon induction, efficient. recombination occurs in all tissues examined; (iii) there is apparently no position effect variegation (PEV) connected with the LC-1 locus.

Considering the rapidly increasing number of mouse lines producing tTA or rtTA in a wide variety of tissues/cell types (for review see ref. 11) and the large "zoo" of mouse lines with loxP-flanked genes (12), the LC-1 line will allow researchers to exploit both pools to generate animals where CRE activity is subjected to Tet control. Eventhough the breeding of triple transgenic mice will be somewhat demanding, it permits, however, to obtain the desired animals without generating and characterizing a new transgenic line.

Material and Methods

DNA Constructs

The bidirectional transcripton unit (FIG. 6) encoding the cre and the luciferase (luc) gene under the control of the promoter $P_{tet}$bi-1 (7,13) was derived as described previously (12). The sequence of the transcription unit is available upon request.

The $P_{LAP}$ rtTA2$^S$-S2 transcription unit (FIG. 6) was obtained by first replacing the SV40 poly A site in pUHrT61-1 (15) by the β-globin intron/poly A sequence. Subsequently, the $P_{CMV}$ sequence was exchanged for the sequence encoding the promoter of the liver enriched activator protein (16) derived from plasmid pUHG15-30 (17). Sequence information for the resulting plasmid pUHrT61-30 is available upon request.

Generation of Transgenic Mice

LC transgenic mice were obtained by by pronuclear injection of a purified 6.8 kb Not 1-fragment containing the bidirectional transcription unit into fertilized F2 (C57Bl/6X BALB/c) eggs. Similary, rTA$^{LAP}$ mice were generated by transferring the 5.1 kb XmnI-AsnI fragment of pUHrT61-30 into fertilized F2 (C57Bl/6X DBA) eggs, following standard techniques (20).

Genotypes were identified by Southern blot analyses and PCR using DNA from tail biopsies. Probes for Southern blot analyses were for LC animals the 1.25 kb Sal I fragment from PtZ19Rcre$^{NLS}$-1 (14) and for rTA$^{LAP}$ mice the 0.75 kb XbaI-BamHI-fragment from pUHrT 61-1.

For PCR analyses, the following primers were designed:

```
luc:
sense luc1:     5' TTA GAG ATG CAC ATA TCG AGG 3'
                (SEQ ID NO: 5)

antisense       5' TAA CCC AGT AGA TCC AGA GG 3'
luc2:           (SEQ ID NO: 6)

cre:
sense Cre3:     5' TCG CTG CAT TAC CGG TCG ATG C 3',
                (SEQ ID NO: 7)
```

```
                        -continued
antisense       5' CCA TGA GTG AAC GAA CCT GGT CG 3'
Cre4:           (SEQ ID NO: 8)

TetR (synthetic):
sense sTA:      5' CCA TGT CTA GAC TGG ACA AGA 3'
                (SEQ ID NO: 9)

antisense sTA:  5' CTC CAG GCC ACA TAT GAT TAG 3'
                (SEQ ID NO: 10)

tetR (native):
sense tet:      5' AAT GAG GTC GGA ATC GAA GG 3'
                (SEQ ID NO: 11)

antisense tet:  5' TAG CTT GTC GTA ATA ATG GCG G 3'
                (SEQ ID NO: 12)
```

Routinely PCR was carried out for 28 cycles and resulting material was analyzed by electrophoresis in agarose (1%).

Doxycycline Treatment

Double or triple transgenic animals were supplied for two weeks with doxycycline hydrochloride via drinking water (5% succrose, 0.2-2 mg Dox/ml) which was exchanged twice a week. For rapid and short-lived induction, 2 mg of Dox in 0.5 ml of 0.9% aqueous NaCl were injected i.p. Depending on the experiment injections were repeated twice in intervals of 24 hrs.

Luciferase Assay

Tissue samples of transgenic animals were processed and luciferase activities determined as described previously (17).

Histology

In situ β-galactosidase staining: Sacrificed mice were perfused first with PBS followed by 4% paraformaldehyde in PBS. Tissue samples were incubated overnight in PBS containing 30% succrose and subsequently frozen on dry ice. To detect lacz expression 20 μm cryosections mounted on glass slides (SuperFrost Plus, Menzel-Gläser) were stained with 4-bromo-3-chloro-2indolyl-b-galactosidase overnight at 37° C. (18). A 0.1% Nuclear fast red-soluton (Certistain, MERCK) in 5% aqueous aluminiumsulfate solution was used for counterstaining. Immunohistochemistry: Brain immunohistochemistry of CRE recombinase was earned out as described by Kellendonk et al. (19). Liver slices were processed as 20 μm cryosections mounted on glass slides.

Results

Generation of a Mouse Line Controlling CRE Recombinase

To facilitate the identification of founder lines where the cre gene is regulated tightly and over a suitable range, the bidirectional promoter $P_{tet}$bi-1 (13) was used to coregulate the cre and the luciferase (luc) gene (FIG. 6). Upon transfer of the respective DNA construct into mice, seven lines were obtained which transmitted the transgene stably. Animals of these lines were crossed with rTA$^{CMV}$-3 mice which produce rtTA in all organs where the activity of the human cytomegalovirus promoter IE ($P_{hCMV}$) is supported (FIG. 7) including muscle, pancreas, thymus, kidney, spleen (17). Monitoring the luciferase activity in the various organs in presence and absence of Dox revealed the LC-1 line (TCL-1, in ref. 14) as a most promising one: In the OFF state, i.e. in absence of Dox, luciferase activity was barely or not at all detected in any organ. By contrast, when Dox was supplied (2 mg/ml in drinking water), it was induced to levels reflecting the activity of $P_{hCMV}$ in the respective organs (FIG. 7). Moreover, when LC-1 mice were crossed with animals of the TA$^{LAP}$-2 line (15), a hepatocyte specific tTA mouse line, luciferase was induced to high levels exclusively in the liver (FIG. 7).

Generation of a Mouse Line Expressing rtTA2$^S$-S2 under the control of the LAP promoter.

The promoter of the liver enriched activator protein P$_{LAP}$ (16) can give rise to hepatocyte specific expression when ectopically inserted in transgenic mice, as previously shown with the mouse lines TA$^{LAP}$-1 and TA$^{LAP}$-2 (17) which produce tTA in a highly hepatocyte specific manner. For various reasons, it was of interest to generate an analogous mouse line that expresses rtTA instead of tTA in hepatocytes. Thus, the fusion between P$_{LAP}$ and the gene encoding the novel transactivator rtTA2s-S2 (15) was used for transgenesis resulting in 7 DNA positive animals of which 5 transmitted the transgene. When crossed with individuals of the LC-1 line, noninvasive luciferase monitoring (21) in presence and absence of Dox (2 mg/ml in drinking water) revealed one line designated rTA$^{LAP}$-1 where the antibiotic induced high activities. When luciferase was measured in extracts of isolated organs of double transgenic rTA$^{LAP}$-1LC-1 mice, high values were, as expected, found in liver, but also in kidney. As seen in FIG. 7, in absence of Dox luciferase values are at the level of instrumental background (~1 rlu/µg protein). Upon induction by Dox, all organ extracts examined show increased luciferase activity which is, however, 2-3 orders of magnitude below the values observed in liver and kidney. Our data show that the luc gene is controlled very tightly in the OFF state in all tissues, while it is activated over more than 3-4 orders of magnitude in liver and kidney, respectively (FIG. 7). Examination of rTA$^{LAP}$-1/nZL-2 double transgenic animals where the lacZ gene is under control of P$_{tet}$bi-1 revealed that every hepatocyte is stained demonstrating that in rTA$^{LAP}$-1 mice P$_{LAP}$ is not subjected to position effect variegation (data not shown). Moreover, induction of luciferase expression in rTA$^{LAP}$-1/LC-1 animals is rapid as luciferase activity can be monitored within 1 hour after i.p. injection of 2 mg of Dox (21).

Doxycycline Controlled CRE Expression

Eventhough it was anticipated that cre and luc are coregulated by Dox (21), the usefulness of the LC-1 mouse line obviously depends on the tightness of CRE expression in the OFF state and the intracellular level of CRE upon induction which would ensure efficient recombination at the target site. By using the R26R (22) indicator mouse line where constitutive beta-galactosidase synthesis via the endogenous ROSA26 promoter is prevented at the transcriptional level by a loxP-stop-loxP sequence, the functional CRE background of the LC-1 mouse line was examined. Thus, LC-1/R26R double transgenic animals were histologically analyzed for beta-galactosidase activity at day E14 of embryonic development (data not shown) and through adulthood. As exemplified in FIG. 8, for six tissues no signs of recombination were detected in up to 14-month-old animals in any tissue examined. These results confirm the tight control of the bidirectional transcription unit in the LC-1 locus as already indicated by the barely detectable luciferase activity.

The same picture emerges when triple transgenic animals, where tTA or rTA is expressed tissue-specifically, are examined in the OFF state. As exemplified for liver, kidney and lung, there is no sign of recombination in rTA$^{LAP}$-1/LC-1/R26R animals in the OFF state (FIG. 9). By contrast, two i.p. injections (2 mg of Dox each) spaced 24 hrs apart convert the inactive lacz into an active configuration within less than 48 hrs. This experiment revealed that in the rTA$^{LAP}$-1 mouse line the transactivator is produced not only in hepatocytes but also in some additional rather well defined cell populations such as the cortical proximal tubules and of TAL profiles of the inner stripe of the kidney as well as in cells lining blood vessels of the lung (FIG. 9). This particular pattern of CRE activity is obviously due to position effects governing the activity of the LAP promoter in the rTA$^{LAP}$-1 mouse line, as comparisons with TA$^{LAP}$-1 and TA$^{LAP}$-2 mouse lines (17) confirm (data not shown). When LC-1 mice were crossed with individuals of the TA$^{CamK}$-1 mouse line (line B in ref. 20) which constitutively produce tTA in neurons of the forebrain, Dox dependent co-regulation of CRE and luciferase expression was demonstrated by assaying luciferase activity and by immunostaining of CRE in situ (FIG. 10).

Accessibility of the LC-1 locus for tTA/rtTA

Detailed analysis of liver sections as depicted in FIG. 9 shows that in rTA$^{LAP}$-1LC-1/R26R animals recombination has occurred in every hepatocyte. Obviously, none of the three mouse lines gives rise to position effect variegation in hepatocytes implying that every hepatocyte produces rtTA which, when activated by Dox, can access the respective LC-1 locus to express CRE which in turn is capable of catalyzing a recombination event at the ROSA26 locus in every cell. Together with the data shown in FIG. 7 these results show that at least in liver the LC-1 mouse line is not subjected to PEV and that CRE levels are induced that lead to a rapid and complete deletion of an appropriately loxP-flanked DNA segment. This reasoning is supported by data obtained with two sets of triple transgenic animals (TA$^{LAP}$-1/LC-1/polb$^{flox}$ and µEG2/LC-1/polb$^{flox}$) where efficient deletion of the loxP-flanked beta polymerase was achieved in hepatocytes and T lymphocytes, respectively (14).

Discussion

Here, two transgenic mouse lines are described of which the first one, the LC-1, allows to superimpose an effective and reliable temporal control onto CRE mediated recombination via the Tet regulatory system, whereas the second one, the rTA$^{LAP}$-1, confines Tet regulation via rtTA rather exclusively to hepatocytes and some subsets of kidney cells.

The LC-1 mouse line will expand the applications of conditional mutagenesis. A prerequisite for regulating a gene of interest such as the cre gene tightly and over a sufficient range is the integration of the P$_{tet}$-cre transcription unit into an appropriate chromosomal site, where no outside activation of P$_{tet}$ occurs while high levels of expression can be achieved upon induction. Indeed, the locus identified in the LC-1 mouse line appears to fulfill all criteria required. First, there is no CRE recombination detectable in any tissue and at any time during development and adulthood of up to 14-month-old LC-1/R26R double transgenic animals demonstrating that the bidirectional cre-luc transcription unit embedded in the LC-1 locus generates no or only subfunctional and, thus, negligible amounts of CRE which agrees with the barely measurable luciferase activities monitored in the various organs of the animals. Corresponding results were obtained with rTA$^{LAP}$-1/LC-1/R26R triple transgenic mice. Thus, in the OFF state the LC-1 locus appears to be ubiquitously silent. Second, expression of CRE and luciferase is inducible in all cell types and tissues examined. For example, by crossing LC-1 mice with individuals of the rTA$^{CMV}$-3 line, luciferase activity is detected in all tissues/organs where P$_{hCMV}$ is known to be active (FIG. 7; 17). Moreover, luciferase is induced in hepatocytes, neurons and kidney cells as analyses of respective LC-1 double transgenic animals show. In the LC-1 locus, the cre and the luciferase gene are transcribed at about the same rate (21). It, therefore, can be safely assumed that CRE is produced in all cells where luciferase can be monitored. This is supported by immunostaining of CRE which was positive in all tissues analyzed, namely in hepatocytes, kidney cells and neurons (FIG. 9, 10). In these latter cell types, efficient CRE mediated recombination was detected via the R26R reporter mouse line. Based on previous experience with several mouse and cell lines containing bidirectional transcription units, it is likely that wherever luciferase can be induced in LC-1 animals, CRE will be expressed as well. Therefore, given the present set of data, it appears not unlikely that LC-1 animals are capable of producing CRE and, thus, of mediating recombination in many, possibly all cell types provided that tTA or rtTA is expressed in the respective cell. Third, the data obtained with $rTA^{LAP}$-1/LC-1/R26R mice show that upon induction of CRE recombination occurs in all hepatocytes. Accordingly, the LC-1 locus is accessible for tTA/rtTA in every cell. Similar results were obtained in pyramidal cells of the hippocampus (R. Sprengel, pers. communication). Apparently, the LC-1 locus does not cause PEV in these very different cell types, and it will be interesting to learn from future studies whether absence of PEV will be another general characteristic of this locus.

The second mouse line characterized here ($rTA^{LAP}$-1) demonstrates that CRE and luciferase controlled by $P_{tet}$bi-1 can be regulated over several orders of magnitude via Dox in highly specific cell populations while not causing any measurable activity of luciferase or CRE in the uninduced state. The finding that in the uninduced state even 6 to 8-month-old triple transgenic animals ($rTA^{LAP}$-1/LC-1/R26R) show no sign of recombination in cells producing $rtTA2^S$-S2 demonstrates the high discrimination potential of this transactivator.

In conclusion, the properties of the genomic site, where the $P_{tet}$bi-1 controlled cre gene is integrated and coregulated with the luc gene, make the LC-1 mouse line an interesting and probably widely applicable experimental tool for controlling CRE recombination in vivo. Moreover, the fact that the expression of CRE cannot only be tightly suppressed, thus preventing undesired background, but also induced to high levels may be of-particular value. Various reports suggest that recombination efficiency also depends on the topography of the loxP-flanked DNA within the chromatin context. Short exposure of such sites to high levels of CRE may be a suitable approach for inducing efficient and complete recombination while avoiding side effects of high constitutive levels of recombinase. Finally, considering the two growing "zoos" of transgenic mouse lines containing either tTA/rtTA genes under the control of various tissue specific promoters or a wide variety of loxP-flanked genes, the LC-1 mouse line provides an attractive link for exploiting the two worlds of transgenic mice.

REFERENCES

1. Rajewsky, K., Gu, H., Kühn, R., Betz, U. A., Müller, W., Roes, J. and Schwenk, F. (1996) Conditional gene targeting. *J. Clin. Invest.*, 98, 600-603.
2. Lewandoski, M.(2001) Conditional control of gene expression in the mouse. *Nat. Rev. Genet.*, 2, 743-755.
3. Kühn, R. and Schwenk, F. (2002) Conditional knockout mice. In van Deursen, J. and Hofker, M. (eds), *The Transgenic Mouse: Methods and Protocols*. Humana Press Inc., USA, pp. 159-186.
4. Thyagarajan, B., Guimaraes, M. J., Groth, A. C. and Calos, M. P. (2000) Mammalian genomes contain active recombinase recognition sites. *Gene*, 244, 47-54.
5. Schmidt, E. E., Taylor, D. S., Prigge, J. R., Barnett, S. and Capecchi, M. R. (2000) Illegitimate Cre-dependent chromosome rearrangements in transgenic mouse spermatids. *Proc. Natl. Acad. Sci. USA*, 97, 13702-13707.
6. Gossen, M. and Bujard, H. (1992) Tight control of gene expression in mammalian cells y tetracycline responsive promoters. *Proc. Natl. Acad. Sci. USA*, 89, 5547-5551.
7. Baron, U. and Bujard, H. (2000) Tet repressor based systems for regulated gene expression in eukaryotic cells: principles and advances. *Methods Enzymol.*, 327, 401-421.
8. Saam, J. R. and Gordon, J. I. (1999) Inducible gene knockouts in the small intestinal and colonic epithelium. *J. Biol. Chem.*, 274, 38071-38082.
9. Utomo, A. R., Nikitin, A. Y. and Lee, W. H. (1999) Temporal, spatial and cell type-specific control of Cre-mediated DNA recombination in transgenic mice. *Nat. Biotechnol.*, 17, 1091-1096.
10. Lindeberg, J., Mattsson, R. and Ebendal, T. (2002) Timing the doxycycline yields different patterns of genomic recombination in brain neurons with a new inducible Cre transgene. *J. Neurosci. Res.*, 68, 248-253.
11. Schönig, K. and Bujard, H. (2002) Generating conditional mouse mutants via tetracycline controlled gene expression. In van Deursen, J. and Hofker, M. (eds), *The Transgenic Mouse: Methods and Protocols*. Humana Press Inc., USA, pp. 69-104.
12. www.mshri.on.ca/nagy/crc.htm
13. Baron, U., Freundlieb, S., Gossen, M. and Bujard, H. (1995) Co-regulation of two gene activities by tetracycline via a bidirectional promoter. *Nucleic Acids Res.*, 23, 3605-3606.
14. Schwenk, F. (1997) PhD Thesis, University of Cologne.
15. Urlinger, S., Baron, U., Thellmann, M., Hasan, M. T., Bujard, H. and Hillen, W. (2000) Exploring the sequence space for tetracycline-dependent transcriptional activators: novel mutations yield expanded range and sensitivity. *Proc. Natl. Acad. Sci. USA*, 97, 7963-7968.
16. Talbot, D., Descombes, P. and Schibler, U. (1994) The 5' flanking region of the rat LAP (C/EBP beta) gene can direct high-level, position-independent, copy number-dependent expression in multiple tissues in transgenic mice. *Nucleic Acids Res.*, 22, 756-766.
17. Kistner, A., Gossen, M., Zimmermann, F., Jerecic, J., Ullmer, C., Lübbert, H. and Bujard, H. (1996) Doxycycline-mediated quantitatie and tissue-specific control of gene expression in transgenic mice. *Proc. Natl. Acad. Sci. USA*, 93, 10933-10938.
18. Hogan, H., Beddington, R., Constantini, F. and Lacy, E. (1994) *Manipulating the Mouse Embryo—A Laboratory Manual.* $2^{nd}$ edition, Cold Spring Harbor Laboratory Press, Cold Spring Harbor, N.Y.
19. Kellendonk, C., Tronche, F., Casanova, E., Anlag, K., Opherk, C. and Schutz, G. (1999) Inducible site-specific recombination in the brain. *J. Mol. Biol.*, 285, 175-182.
20. Mayford, M., Bach, M. E., Huang, Y. Y., Wang, L., Hawkins, R. D. and Kandel, E. R. (1996) Control of memory formation through regulated expression of a CamKII transgene. *Science*, 274, 1678-1683.
21. Hasan, M. T., Schönig, K., Berger, S., Graewe, W. and Bujard, H. (2001) Longterm, noninvasive imaging of regulated gene expression in living mice. *Genesis*, 29, 116-122.
22. Soriano, P. (1999) Generalized lacZ expression with the Rosa26 Cre reporter strain. *Nat. Genet.*, 21, 70-71.

The invention claimed is:

1. A method for constructing a vector for transgenesis into the genome of a mammalian cell or a mammalian organism, said method comprising introducing between a first flanking sequence comprising SEQ ID NO: 1 and SEQ ID NO:4 of the mouse LC-1 locus and having a length of 5 kbp to 150 kbp and a second flanking sequence comprising SEQ ID NO: 2 and SEQ ID NO:3 of the mouse LC-1 locus and having a length of 5 kbp to 150 kbp in said vector at least one transcription unit containing a gene to be introduced into the genome.

2. A vector for transgenesis into the genome of a mammalian cell or a mammalian organism, said vector comprising, in order: i) a first flanking sequence comprising SEQ ID NO: 1 and SEQ ID NO:4 of the mouse LC-1 locus and having a length of 5 kbp to 150 kbp, ii) at least one transcription unit containing a gene to be introduced into the genome, and iii) a second flanking sequence comprising SEQ ID NO: 2 and SEQ ID NO:3 of the mouse LC-1 locus and having a length of 5 kbp to 150 kbp.

3. The vector of claim 2, wherein the transcription unit comprises a multimer of tetO flanked on each side by a construct comprising an enhancerless promoter and a gene of interest.

4. The vector of claim 3, wherein the genes of interest encode luciferase and cre recombinase, respectively.

5. The vector of claim 2, characterized in that the vector comprises a first transcription unit and a second transcription unit spaced by a sequence of sufficient length to prevent any influence of transcription factors that bind to one of the transcription units on the transcription of the respective other transcription unit, said first transcription unit comprising one or more genes of interest and one or more transcription control sequences, the transcription of the genes of interest being susceptible to control by the binding of a transactivator to the transcription control sequences, and said second transcription unit comprising a gene encoding a transactivator.

6. The vector of claim 2, wherein said mammalian organism is a rat or a mouse.

* * * * *

UNITED STATES PATENT AND TRADEMARK OFFICE
CERTIFICATE OF CORRECTION

PATENT NO. : 7,666,668 B2 Page 1 of 1
APPLICATION NO. : 10/525785
DATED : February 23, 2010
INVENTOR(S) : Bujard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1067 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,666,668 B2  Page 1 of 1
APPLICATION NO. : 10/525785
DATED : February 23, 2010
INVENTOR(S) : Hermann Bujard et al.

It is certified that error appears in the above-identified patent and that said Letters Patent is hereby corrected as shown below:

Column 1, after line 9, insert --DESCRIPTION--;

Column 9, line 53, "LG-1" should read --LC-1--;

Column 15, line 54, "PtZ19Rcre$^{NLS}$-1" should read --PTZ19Rcre$^{NLS}$-1--;

Column 17, line 11, "rtTA2s-S2" should read --rtTA2$^s$-S2--;

Column 17, line 18, "rTA$^{LAP}$-1LC-1" should read --rTA$^{LAP}$-1/LC-1--; and

Column 18, line 17, "rTA$^{LAP}$-1LC-1/R26R" should read --rTA$^{LAP}$-1/LC-1/R26R--.

Signed and Sealed this
Twelfth Day of April, 2011

David J. Kappos
*Director of the United States Patent and Trademark Office*

SEQUENCE LISTING

<160> NUMBER OF SEQ ID NOS: 12

<210> SEQ ID NO 1
<211> LENGTH: 207
<212> TYPE: DNA
<213> ORGANISM: Artificial sequence
<220> FEATURE:
<223> OTHER INFORMATION: Partial sequence of the E11 insert obtained by
      probing E11 DNA with primer 3 initiating DNA synthesis from
      sequences within the vector pBeloBAC.

<400> SEQUENCE: 1
taaagggaaa tccacaattt aaaatgtgac agaaatttat gattgttttt atttaaatgt    60
ttatcttttc aagaaatatc acgtgtaatg tatttcaaaa tgtctcctag aaaagtgcat   120
gactctgcga aggagagagt tggtggggga gagtcaggaa aatgtagagg ggcaacaatg   180
tagaaattat ggaaaatgaa attaata                                       207

<210> SEQ ID NO 2
<211> LENGTH: 420
<212> TYPE: DNA
<213> ORGANISM: Artificial sequence
<220> FEATURE:
<223> OTHER INFORMATION: Partial sequence of the E11 insert obtained by
      probing E11 DNA with primer 3 initiating DNA synthesis from
      sequences within the vector pBeloBAC : Subclone 5.

<400> SEQUENCE: 2
actataccat acttgattta aacatattag cagtttctct ccttcattat gtactccgct    60
aaatttgaat atgaaaccat tcttgtacca ctgacagttg gcagaaagtt tactttataa   120
acacattttt aagcatgtgt atatgtatgt gtatgtgtgg ttatgtgtac agaattgcaa   180
gtgccccaag agaccctagg tctggagtta caggtggctg taaggtggca attgaactct   240
gatcctctgc aagggcatgc atgctcttaa ccattgagcc atccctactg cctggcaaca   300 agttttttgat agcaactttt atcctgttgg atgaactgaa aaccgggcaa aattctgtgt   360
ctggtcctaa acatgtttgt acttatgaag aacttttccc aatttttttg ggaaaatgtt   420

<210> SEQ ID NO 3
<211> LENGTH: 81
<212> TYPE: DNA
<213> ORGANISM: Artificial sequence
<220> FEATURE:
<223> OTHER INFORMATION: Partial sequence of the E11 insert obtained by
      probing E11 DNA with primer T7 initiating DNA synthesis from
      sequences within the vector pBluescript: Subclone BAC22.

<400> SEQUENCE: 3
gcctgagcat cggtgacaga catcttggtt ccgggactcc accctgagtg ttctgcacag    60
gtgagagtgt ggaatacagg g                                              81

<210> SEQ ID NO 4
<211> LENGTH: 483
<212> TYPE: DNA
<213> ORGANISM: Artificial sequence
<220> FEATURE:
<223> OTHER INFORMATION: Partial sequence of the E11 insert obtained by
      probing E11 DNA with primer T7 initiating DNA synthesis from
      sequences within the vector pBluescript: Subclone BAC18.

<400> SEQUENCE: 4
gtgactgttc aaatgctatg cctgactgct ggtcaataat gctccctgtc atgatgataa    60

```
ttggtgacct tctgcaaatg tagacaaggc accaacagtt agatgtttcc ttttatgtgt    120
tgccttggtc atgatatctc tttacaccaa tagaaaagta aataagatat ctatctaagc    180
tcacattata tcttggaaca ggaagcacgt ctgttacctc tatccacctg acctcattcc    240
tcttaagaca tctctaacct ctagacataa ttcactatac acacagttct tctcttctgc    300
caaatctgct ccttcaataa caaactcaaa aataacaatg tccacatgca cagatctcct    360
ctcagaaata ccaacaatat gaaagatgaa gccagcatct tctctccaaa acttgtagaa    420
atgtttacca ataagaacca catagatgaa caaaggaaac agaatttaga agagcaatta    480
taa                                                                  483

<210> SEQ ID NO 5
<211> LENGTH: 21
<212> TYPE: DNA
<213> ORGANISM: Artificial sequence
<220> FEATURE:
<223> OTHER INFORMATION: Primer: luc: sense luc1

<400> SEQUENCE: 5
ttacagatgc acatatcgag g                                              21

<210> SEQ ID NO 6
<211> LENGTH: 20
<212> TYPE: DNA
<213> ORGANISM: Artificial sequence
<220> FEATURE:
<223> OTHER INFORMATION: Primer: luc: antisense luc2

<400> SEQUENCE: 6
taacccagta gatccagagg                                                20

<210> SEQ ID NO 7
<211> LENGTH: 22
<212> TYPE: DNA
<213> ORGANISM: Artificial sequence
<220> FEATURE:
<223> OTHER INFORMATION: Primer: cre: sense Cre3

<400> SEQUENCE: 7
tcgctgcatt accggtcgat gc                                             22

<210> SEQ ID NO 8
<211> LENGTH: 23
<212> TYPE: DNA
<213> ORGANISM: Artificial sequence
<220> FEATURE:
<223> OTHER INFORMATION: Primer:cre: antisense Cre4

<400> SEQUENCE: 8
ccatgagtga cgaacctgg tcg                                             23

<210> SEQ ID NO 9
<211> LENGTH: 21
<212> TYPE: DNA
<213> ORGANISM: Artificial sequence
<220> FEATURE:
<223> OTHER INFORMATION: Primer: TetR (synthetic): sense sTA

<400> SEQUENCE: 9
ccatgtctag actggacaag a                                              21

<210> SEQ ID NO 10
```

```
-continued
<211> LENGTH: 21
<212> TYPE: DNA
<213> ORGANISM: Artificial sequence
<220> FEATURE:
<223> OTHER INFORMATION: Primer: TetR (synthetic): antisense sTA

<400> SEQUENCE: 10
ctccaggcca catatgatta g                                              21

<210> SEQ ID NO 11
<211> LENGTH: 20
<212> TYPE: DNA
<213> ORGANISM: Artificial sequence
<220> FEATURE:
<223> OTHER INFORMATION: Primer: tetR(native): sense tet

<400> SEQUENCE: 11
aatgaggtcg gaatcgaagg                                                20

<210> SEQ ID NO 12
<211> LENGTH: 22
<212> TYPE: DNA
<213> ORGANISM: Artificial sequence
<220> FEATURE:
<223> OTHER INFORMATION: Primer: tetR(native): antisense tet

<400> SEQUENCE: 12
tagcttgtcg taataatggc gg                                             22
```